US012721559B2

(12) United States Patent
Gao et al.

(10) Patent No.: US 12,721,559 B2
(45) Date of Patent: Sep. 1, 2026

(54) PHYSICOCHEMICAL-SENSING ELECTRONIC SKIN FOR STRESS RESPONSE MONITORING

(71) Applicant: CALIFORNIA INSTITUTE OF TECHNOLOGY, Pasadena, CA (US)

(72) Inventors: Wei Gao, Pasadena, CA (US); Changhao Xu, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 175 days.

(21) Appl. No.: 18/755,391

(22) Filed: Jun. 26, 2024

(65) Prior Publication Data

US 2025/0000414 A1 Jan. 2, 2025

Related U.S. Application Data

(60) Provisional application No. 63/523,443, filed on Jun. 27, 2023.

(51) Int. Cl.

| | |
|---|---|
| *A61B 5/16* | (2006.01) |
| *A61B 5/00* | (2006.01) |
| *A61B 5/145* | (2006.01) |

(52) U.S. Cl.

CPC ............ *A61B 5/165* (2013.01); *A61B 5/0002* (2013.01); *A61B 5/14521* (2013.01); (Continued)

(58) Field of Classification Search

CPC ...................................................... A61B 5/165

See application file for complete search history.

(56) References Cited

U.S. PATENT DOCUMENTS 8,790,259 B2 * 7/2014 Katra ..................... A61B 5/746 600/301

2018/0317833 A1 11/2018 Heikenfeld et al.

(Continued)

FOREIGN PATENT DOCUMENTS

WO 2016/197116 A1 12/2016

WO 2022/170361 A1 8/2022

OTHER PUBLICATIONS

Wenhui, Ji et al., "Wearable Sweat Biosensors Refresh Personalized Health/Medical Diagnostics," Research, A Science Partner Journal, vol. 2021, Oct. 22, 2021. (Year: 2021).*

(Continued)

*Primary Examiner* — Michael Fuelling

(74) *Attorney, Agent, or Firm* — Sheppard Mullin Richter & Hampton LLP

(57) ABSTRACT

Systems and methods for a wearable stress response assessment system may include an iontophoresis module, a multi-inlet microfluidic sweat sampling component, and a sensor patch configured to detect concentrations of electrolytes and metabolites present in a sweat sample and monitor physiological signs prevalent in a human patient. An iontophoresis module may provide for stimulation of a biofluid sample. A biofluid may be a sweat sample. Stimulation may be achieved via electrostimulation and/or application of a stimulating agent. A microfluidic sweat sampling component may include adhesive and PDMS layers with carefully designed inlets and channels for efficient collection and sampling of biofluid. Enzymatic and ISE biosensors may quickly and accurately identify concentrations of key biomarkers present in a biofluid sample which may assess, in combination with monitored physiological signs, a human patient's stress response.

6 Claims, 13 Drawing Sheets

(52) U.S. Cl.
CPC ........ *A61B 5/14546* (2013.01); *A61B 5/4866* (2013.01); *A61B 5/6833* (2013.01); *A61B 5/7264* (2013.01); *A61B 2562/12* (2013.01)

(56) References Cited

U.S. PATENT DOCUMENTS

| | | | | |
|---|---|---|---|---|
| 2020/0093416 | A1 | 3/2020 | Rogers et al. | |
| 2021/0076988 | A1* | 3/2021 | Wang .................. | A61B 5/1486 |
| 2023/0157592 | A1 | 5/2023 | Gao et al. | |

OTHER PUBLICATIONS

PCT International Search Report and the Written Opinion mailed Nov. 6, 2024, issued in related International Application No. PCT/US2024/035672 (18 pages).

Sun Teng et al., "A low-cost and simple-fabricated epidermal sweat patch based on "cut-and-paste" manufacture", Sensors and Actuators B: Chemical, Elsevier BV, NL, vol. 368, Jun. 9, 2022.

* cited by examiner

PHYSICOCHEMICAL-SENSING ELECTRONIC SKIN FOR STRESS RESPONSE MONITORING

RELATED APPLICATION

This application claims the benefit of U.S. Provisional Application No. 63/523,443 filed on Jun. 27, 2023, the contents of which are incorporated herein by reference in their entirety.

This invention was made with government support under Grant No. NNX16A069A awarded by NASA and under Grant No. N00014-21-1-2483 awarded by the Office of Naval Research. The government has certain rights in the invention.

TECHNICAL FIELD

The present disclosure relates generally to wearable sensors for stress monitoring. In particular, some implementations may relate to systems and methods for physicochemical-sensing electronic skin for stress response monitoring using human sweat samples.

BACKGROUND

Stress is a complex concept that has often been used to capture a wide range of phenomena. For example, the term "stress" has at times been used to refer to life events or experiences that occur to individuals (e.g., the break-up of a romantic relationship, losing one's job) and at other times to refer to the response to these types of experiences. Given the broad ways in which the term "stress" has often been used, there have been calls to increase the specificity with which aspects of stress (e.g., stimulus, response) are defined. This disclosure focuses on "stress" as the stress response, which occurs when demands placed on an individual exceed their resources to manage those demands. However, systems and methods disclosed herein may be applied to other "stress"-inducing situations.

Stress responses can occur across multiple levels and systems, including cognitive, affective, behavioral, and biological processes. The stress response is relevant to a wide range of mental and physical health outcomes, including depression, anxiety disorders, and cardiovascular disease. In contrast to the stress response, a stressor is an exposure (e.g., stressful event or stimulus) that triggers this response.

Approaches to quantify stress responses typically rely on subjective surveys and questionnaires. To account for this, wearable sensors can potentially be used to continuously monitor stress-relevant biomarkers. However, the biological stress response is spread across the nervous, endocrine, and immune systems, and the capabilities of conventional sensors are not sufficient for condition-specific stress response evaluation.

Wearable bioelectronic technology/devices (including wearable sensors) offer many advantages for personalized health monitoring. Wearable devices are non-invasive and present less user error than other monitoring methods. Additionally, wearable devices offer the potential to monitor health status over time as opposed to collecting a sample that reflects health status at only a snap shot in time. This type of real-time monitoring offers more accurate and individualized diagnosis, treatment, and prevention for health conditions. Specifically, wearable devices can measure pulse, respiration rate, temperature, and other health status indicators.

Sweat sensors are one type of wearable bioelectronic sensors that are particularly desirable because sweat contains many key biomarkers including electrolytes, metabolites, amino acids, hormones, and drug levels. However, existing sweat sensors face several key problems. First, existing sensors lack an effective continuous monitoring strategy. They employ sensors that are only able to measure a limited set of biomarkers. This limited set of biomarkers alone does not provide a full enough picture of a human subject's health status to serve as an effective stress assessment tool. Additionally, these sensors often require a large sample of sweat to provide accurate analysis of biomarkers. This requires a larger and more powerful device, which may not be suitable as a wearable. Therefore, monitoring, and especially continuous monitoring presents a challenge due to the need for high power and for power storage. Existing models present additional challenges including that they require complex fabrication, are difficult to reproduce in large quantities in an affordable way, and are fragile, making them not suitable as wearable devices for long periods.

For at least these reasons, the current "gold standard" for measuring biomarkers in the body is blood testing. Blood testing has several drawbacks including that it is invasive, as it requires withdrawal of blood from the veins. Also, accurate blood testing, and/or blood testing generally, needs larger samples, generally requiring a human patient to come to the lab and be tested. Because of the lab requirement and invasiveness, blood testing is generally only performed at a snapshot or discrete moment in time. This means that in many cases, unless a patient is experiencing a flare up or other type of health episode at the time of testing, the testing may not reveal any unusual biomarker levels until a health problem has become severe. Additionally, this episodic testing makes it extremely difficult to determine what factors may influence a patient's change in stress levels over time. Further, blood testing is very delicate as samples can be easily compromised by oxidation and other factors. Therefore, expensive equipment is required to process each sample, resulting in lengthy processing times and less testing overall.

Because of the lack of effective continuous monitoring strategies and high power needs, currently existing wearable health monitoring systems are unable to measure key biomarkers in a way sufficient to monitor stress response. An effective wearable system would be highly desirable as a mechanism for assessing stress as the current alternatives are invasive, expensive, and offers limited health information over time.

SUMMARY

Systems and methods are described herein related to wearable assessment systems capable of continuous health monitoring and stress response assessments. Health monitoring and stress assessments may include detecting concentrations of key electrolytes and metabolites, as well as, monitoring physiological indicators, such as vital signs. Such detecting and monitoring may support stress response assessments. Such a system may leverage several strategies including integration of a sweat sensor patch adapted to adhere to and induce sweat production from a human patient's skin. The sweat sensor patch may be coupled to a microfluidic sampling component that includes multiple inlets that contact the human patient's skin and are configured to collect a sweat sample from the human patient's skin. The microfluidic sweat sampling component coupled to the sweat sensor patch may further channel the collected sweat to various sensors integrated into the wearable assessment system.

In embodiments, the wearable assessment system may include a metabolite detection logical circuit, which may include a metabolite sensor to identify concentrations of target metabolites in the sweat sample. In such embodiments, the metabolite sensor may be an enzymatic sensor. In embodiments, the wearable assessment system may include an electrolyte detection logical circuit, which may include an electrolyte sensor to identify concentrations of target electrolytes in a sweat sample. In such embodiments, the electrolyte sensor may be an ISE.

In further embodiments, the wearable assessment system may include a physiological indicator logical circuit, which may include various sensors that monitor vital signs from the human patient's skin.

The combination of such logical circuits may input data representative of said detections or monitoring into a smart device with one or more processors and machine-readable instructions embedded thereon. The machine-readable instruction may cause the one or more processors to analyze the detected metabolite concentrations, the detected electrolyte concentrations, and/or the identified physiological signs, and to subsequently display an assessment on a graphical user interface.

In further embodiments, the wearable assessment system's sensor patch may be a multilayered sensor patch that further includes a sweat-stimulation electrode, an enzymatic biosensor, an ion selection sensor (ISE), a capacitive pulse sensor, a resistive galvanic skin response (GSR) sensor, and a skin temperature sensor.

In further embodiments, the wearable assessment system may include a sensor patch where said sensor patch has a top and bottom layer fabricated through serial inkjet printing of silver and carbon, and a middle polydimethylsiloxane (PDMS)-based airgap layer, wherein said PDMS-based airgap layer is spin-coated between the top and bottom layers.

In further embodiments, the wearable assessment system may include a microfluidic sweat sampling component that further includes at least one of: a carbachol hydrogel-loaded sweat-stimulation electrode and/or a hydrogel-loaded sweat-stimulation electrode, wherein either/each electrode may be configured to induce sweat production.

In further embodiments, the wearable assessment system may include a metabolite detection logical circuit that may be configured to identify concentrations of glucose, lactate, and uric acid (UA) in a collected sweat sample. Similarly, the wearable assessment system may include an electrolyte detection logical circuit that may be configured to identify concentrations of $Na^+$, $K^+$, and $NH_4^+$ in a collected sweat sample. Further, the wearable assessment system may include a physiological indicator logical circuit that may be configured to identify signals representative of pulse waveform, galvanic skin response (GSR), and skin temperature from the human patient's skin.

In further embodiments, the wearable assessment system may make the stress assessment based on the analyzed metabolite concentrations, electrolyte concentrations, and physiological signs.

Embodiments of the present wearable stress response assessment system may further include a multilayer sweat sensor patch adapted to adhere to and induce sweat production from a human patient's skin. The multilayer sweat sensor patch may further include a carbochol hydrogel-loaded sweat-stimulation electrode, a hydrogel-loaded sweat-stimulation electrode, three enzymatic biosensors, and three ion-selective sensors (ISEs). In such embodiments, the carbochol-hydrogel-loaded sweat-stimulation electrode and the hydrogel-loaded sweat-stimulation electrode may be integrated into a skin-interfaced laser-engraved microfluidic component, wherein the skin-interfaced laser-engraved microfluidic component may collect an induced sweat sample for analysis. In further embodiments, the three enzymatic biosensors may be integrated into a metabolite detection logical circuit that is further integrated within the sensor patch, wherein each enzymatic biosensor is configured to identify concentrations of one of glucose, lactate, and uric acid (UA) in the collected sweat sample. In further embodiments, the three ion-selective sensors (ISEs) may be integrated into an electrolyte detection logical circuit that is further integrated within the sensor patch, wherein each ion-selective sensor may be configured to identify concentrations of one of $Na^+$, $K^+$, and $NH4^+$ in the collected sweat sample.

In some embodiments, the three enzymatic biosensors may each include an electrodeposited gold nanoparticles layer, an electrodeposited Prussian blue transduction layer, an electrodeposited nickel hexacyanoferrate (NiHCF) protection layer, and an enzyme layer in a glutaraldehyde-crosslinked bovine serum albumin (BSA) matrix.

In some embodiments, the wearable assessment system may further include a smart device, wherein the smart device may analyze the detected metabolite concentrations, and the detected electrolyte concentrations, and display a stress assessment on a graphical user interface based on the analyzed metabolite concentrations and analyzed electrolyte concentrations. In various embodiments, the stress assessment may be determined using machine learning models and/or methods. Additionally, in embodiments, the wearable stress assessment system may further include an in situ signal processing and wireless communication module.

In some embodiments, the three enzymatic biosensors may further include a diffusion-limiting membrane layer that further tunes metabolite detections ranges for high concentration detection. In further embodiments, the three ion-selective sensors (ISEs) may include a carbon layer and a polystyrene-block-poly (ethylene butylene)-block-polystyrene (SEBS)-polyvinyl chloride (PVC)/bis(2-ethylhexyl) sebacate (DOS)-ionophore/lipophilic anionic sites mixture based membrane layer.

Various embodiments may also include a method for determining a stress assessment. The method may include applying a stimulating agent to a human sweat gland where the stimulating agent induces production of sweat. The method may also include collecting an induced sweat sample in a microfluidic sweat sampling component where the microfluidic sweat sampling component channels the collected sweat sample into a metabolite reservoir and an electrolyte reservoir. The method may also include identifying metabolite concentrations in the collected sweat sample via the metabolite detection logical circuit, wherein the metabolite detection logical circuit retrieves a first collected sweat sample from the metabolite reservoir. The method may also include identifying electrolyte concentrations in the collected sweat sample via an electrolyte detection logical circuit, wherein the electrolyte detection logical circuit retrieves a second collected sweat sample from the electrolyte reservoir. The method may also include transmitting information representative of the identified metabolite and electrolyte concentrations to a smart device. The method may also include identifying physiological signals on the human sweat gland via a physiological indicator logical circuit, wherein the physiological indicator logical circuit identifies signals representative of pulse waveform, galvanic skin response (GSR), and skin temperature.

In some embodiments, the stimulating agent applied in this method may be carbachol hydrogel or hydrogel.

In some embodiments, the smart device displays a stress assessment based on the identified metabolite and electrolyte concentrations, and physiological signals. In some embodiments, the stress assessment may be determined using machine learning.

Other features and aspects of the disclosure will become apparent from the following detailed description, taken in conjunction with the accompanying drawings, which illustrate, by way of example, the features in accordance with various embodiments. The summary is not intended to limit the scope of the invention, which is defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 4B is an example diagram showing the schematics of an example inkjet printing mechanism, in accordance with various embodiments of the disclosed technology.

FIG. 4C is an example diagram showing an array of wearable assessments systems fabricated via mass-producible and low-cost inkjet printing, in accordance with various embodiments of the disclosed technology.

Figure 1A:
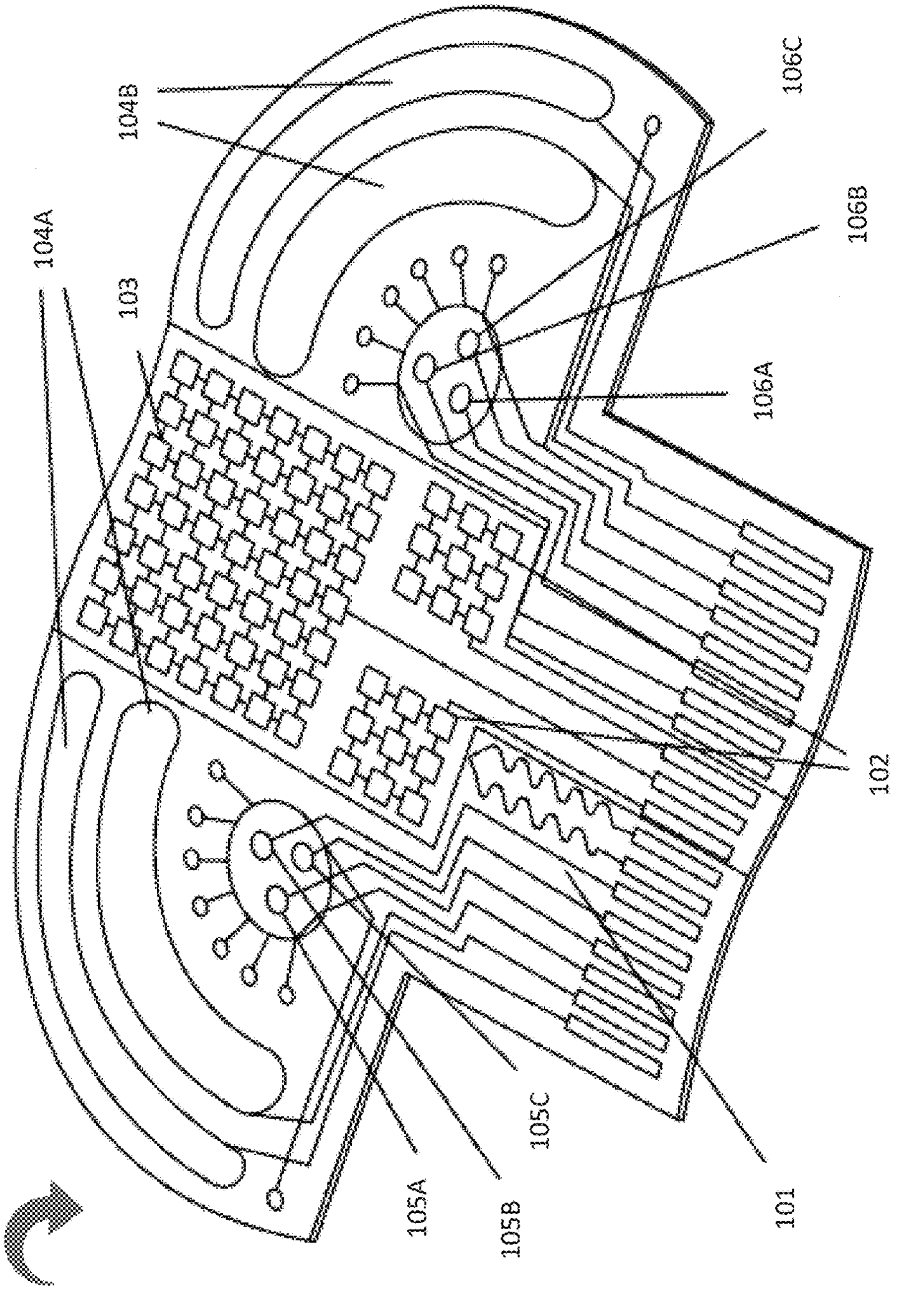
FIGS. 1A-1B are example diagrams showing a wearable assessment system, in accordance with various embodiments of the disclosed technology.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION

Wearable devices may offer highly desirable, non-invasive, and continuous monitoring of key health indicators. One type of desirable wearable device is a sweat sensor. A carefully designed sweat sensor may be particularly desirable because it may allow continuous, on body monitoring of key health indicators. This kind of continuous analysis may allow for personalized medical care and monitoring for an individual based on that individual's particular biomarkers. Biomarkers relevant for stress monitoring and similar assessments may be spread across the nervous, endocrine, and immune systems. Applications for a wearable assessment system using an electronic skin may non-invasively monitor vital signs (e.g., pulse waveform, galvanic skin response, skin temperature, etc.), molecular biomarkers in human sweat (e.g., glucose, lactate, uric acid, sodium ions, potassium ions, ammonium, etc.), and other biomarkers indicative of a stress response. Such applications for a wearable assessment system using a sweat sensor patch may include dietary/nutrition intake monitoring, evaluation of stress and central fatigue, evaluation for risk of metabolic syndrome, evaluation for risk of severe viral infection, including COVID-19, and many other forms of monitoring that may benefit from a continuous stress assessment.

Stress may be a process triggered by demanding physical or psychological events and may cause anxiety as a prototypical psychological response. Although acute stress responses in healthy individuals can be adaptive and manageable, persistent experiences of stress can have deleterious effects on mental and physical health, and many mechanisms behind the stress response are yet unknown. In the United States alone, more than 50 million adults suffer from depression, stress, and anxiety, and after the onset of the COVID-19 pandemic, the number of people suffering from these mental health challenges has drastically risen, causing a heavy burden on the healthcare system. Elevated levels of stress and anxiety also pose a large burden to high-demand occupation workers such as athletes, soldiers, first responders, aviation personnel, and others, potentially interfering with their cognitive performance and decision-making process. In response to these effects, understanding and evaluating the stress response has become an important aspect of clinical healthcare. However, current standards for conventional clinical stress response assessments rely on surveys and performance evaluations, which can be highly subjective and fail to regularly/continuously monitor human patients over time. Thus, there is a need to develop a more efficient and effective stress assessment tool that may not be characterized by these limitations.

Recent advances in wearable sensors have enabled real-time and continuous monitoring of physical vital signs. Through in situ human sweat analysis, wearable biosensors can provide insight/information about an individual's health at the molecular level. However, various challenges remain to be addressed before such sensors can be of use in clinical applications. For example, a limited set of physical signals may not be sufficient for condition-specific assessment of psychological and physiological stress. As such, existing wearable biochemical sensors suffer from poor operation stability in biofluids, which may preclude reliable long-term continuous monitoring. Furthermore, access to human sweat usually requires physical activity that itself can affect an individual's stress and despite recent progress on stress hormone analysis, continuous monitoring of sweat stress hormones at physiologically relevant levels using wearable sensors had not previously been achieved due to the hormones' extremely low concentrations.

Non-invasive biomarkers may be a reliable alternative for monitoring stress response because of the interdependencies between biological and psychological stress. In particular, as discussed, stress may induce a complex biological response in the nervous, endocrine, and immune systems. The perception of stress may activate the hypothalamic-pituitary-adrenal (HPA) axis and sympathetic adrenal medullary (SAM) axis from the hypothalamus in the brain. Acetylcholine in nerve fibers from both axes can stimulate the adrenal gland, releasing stress hormones (for example, epinephrine, norepinephrine, and cortisol) into the blood. Acetylcholine can also activate sudomotor neurons connected to sweat glands that release an ion-rich fluid. This sympathetic activity can be indirectly measured through the galvanic skin response (GSR) and sweat electrolyte levels. The released stress hormones can also inhibit insulin production, affecting the synthesis of metabolites such as glucose, lactate, and uric acid (UA), as well as narrow arteries, boosting cardiac activities. By monitoring these stress-relevant or key biomarkers, it is possible to develop a comprehensive and objective health profile relating biophysical and biochemical signals to dynamic stress response and/or assessment monitoring.

In embodiments of the present disclosure, the wearable assessment system may monitor six molecular biomarkers (e.g., glucose, lactate, UA, $Na^+$, $K^+$, and $NH_4^+$) and three physiological biomarkers (e.g., pulse, GSR, skin temperature). These biomarkers may be used because of their association with stress responses, however, other biomarkers may also be used based on their individual or combined association with stress response. These biomarkers may be selected individually or combined for monitoring and analyzing stress response for at least the reasons outlined below:

Pulse. The neurotransmitter acetylcholine can cause the stimulation of the nerves connected to the skeletal muscles and muscles involved in cardiovascular and respiratory function, which can result in an amplified force output by skeletal muscles and an escalated pace of both heart and breathing rate. In the cardiovascular system, there are beta-1, beta-2, alpha-1, and alpha-2 adrenergic receptions: beta-1 adrenergic receptors can be expressed in the heart and can increase heart rate as well as contractility; beta-2 adrenergic receptions can mainly be expressed in vascular smooth muscle and skeletal muscle that may increase blood perfusion to target organs; alpha-1 and alpha-2 adrenergic receptions may be expressed in vascular smooth muscle that can elicit vasoconstriction.

Galvanic skin response (GSR). Activation of SAM axis in a stress environment can promote eccrine glands' secretion to generate sweat on the skin. GSR can measure skin resistance between two electrodes, and may be an important vital sign that monitors skin conductance changes from the variation of the ionic permeability of sweat gland membranes generated by the sympathetic activity, which can be related to stress arousal and cognitive states. Therefore, identification of the phasic component of GSR can allow for quantification of stress. The sweating response related to stress may be reported mainly in the hands, wrists, arms, and feet where the sweat glands exist densely, which is not directly associated with environmental temperature, but instead may be associated with stressors.

Skin temperature. Activation of muscle activity as well as the stimulation of eccrine sweat may cause a change in skin temperature, and psychological stress may also affect body temperature. Psychogenic fever (e.g., a stress-induced fever) may be a common psychosomatic disease for which skin temperature can be an indicative biomarker. Further, in addition to skin temperature being used as a biomarker that may be indicative of stress, skin temperature can also have an impact on the signals of other biosensors (e.g., enzyme-based sensors), and thus the skin temperature data may also be used to perform biosensor calibration.

Glucose. In addition to physical stress response, stress hormones may also induce metabolic changes in a living organism. The secretion of epinephrine and norepinephrine from the adrenal gland can stimulate glycogenolysis and promote gluconeogenesis in the liver, which can break down glycogen stored by the liver into glucose, and may promote glucose synthesis from non-carbohydrate precursors to enhance the energy necessary for cellular respiration. The stress hormone cortisol may also promote gluconeogenesis and inhibit insulin production to prevent glucose from being stored. Metabolic biomarkers such as glucose have been identified for chronic stress, and elevated levels of fasting glucose as well as post loaded glucose have been found in chronic stress that can cause diabetes. Accordingly, increased levels of glucose have been statistically associated with perceived work stress, and increases in glucose can also be observed in animal models under acute physical and emotional distress.

Lactate. Muscle and brain exertion during stress can transform glucose into lactate as a metabolic product through anaerobic glycolysis. While increased lactate levels can be obtained through long-term muscle exercise in the absence of oxygen, it has also been observed recently that lactate plays a role at the level of the central nervous system. Lactate can also be an important energy substrate in astrocytes, and the increase in lactate after acute exhaustive exercise can be associated with cognitive domains such as working memory and stress, in order to serve as a neuromodulator and protect the central nervous system from stress. Elevated lactate can be observed in venous blood after both physical and psychological stress tests.

Uric acid (UA). UA is another endogenous compound that can impact the stress response. UA levels can impact brain regions that underlie stress reactivity and emotion regulation, and therefore can regulate psychosocial stress and anxiety. Elevated UA can be associated with daily stress, body anxiety, and burnout. Increased UA is also observed in patients with chronic stress and mental disorders.

Sodium ions. The central nervous system can be implicated in electrolyte balance and blood pressure regulation. Sweat electrolytes, for example $Na^+$, can be important biomarkers for sweat rate indicators. Sodium concentration can also be an indicator of hydration state, which can control acute stress response. An increase in sweat sodium concentration can be due to exercise-induced stress, as well as mental stress. Stress may also cause pressure natriuresis, where inadequate increases in urinary sodium excretion in response to stress-induced blood pressure increases occur.

Potassium ions. $Na^+$—$K^+$ pump regulation can be an important mechanism that can control skeletal muscle contractility. Stress hormones such as epinephrine can induce acute hypokalemia in plasma. Potential stress biomarkers also can play a role in the prognosis and therapy guidance of stress-related diseases and disorders, such as obesity, inflammatory, and cardiovascular diseases. For example, both $K^+$ and $NH_4^+$ can correlate with cardiovascular health and fatigue.

Ammonium ions. Ammonium can appear in the blood mainly due to the breakdown of protein. Psychosocial stress can negatively affect liver metabolism and contribute to the worsening progression of hepatic diseases, while ammonium may be a biomarker since the liver converts ammonia to urea prior to its excretion. Ammonium ions along with lactate can accumulate during graded exercise in humans.

Turning now to the wearable stress response assessment system (also described as the wearable assessment system throughout). The wearable assessment system may include various biosensors, including, for example, enzymatic biosensors, ion selection sensors (ISEs), and physiological biosensors or indicators. Molecular biosensors (e.g., enzymatic biosensors, ISEs, metabolic biosensors, electrolyte biosensors, etc.) may be configured to detect a wide variety of organic compounds present in a sweat sample, such as metabolites, electrolytes, amino acids, vitamins, minerals, hormones, antibodies, and other compounds that may be present in a sweat sample (at minimally sufficient levels where biosensors may detect concentrations of each compound). Generally, biosensors may include enzymatic sensors, ISEs, tissue-based sensors, antibody sensors, DNA sensors, optical sensors, capacitive pulse sensors, electrochemical biosensors, GSR sensors, temperature sensors, piezoelectric sensors, and/or similar biosensors.

Several electrochemical sensing strategies based on enzymes, ionophores, molecularly imprinted polymers, aptamers, and antibodies may be included in the wearable assessment system. This is novel in the field, as existing wearable chemical sensors demonstrate large sensor drifts when these conventional sensors are used in body fluids, which hinders the long-term continuous usability of the conventional wearable chemical sensors for assessments and monitoring using sweat samples.

Furthermore, conventional wearable enzymatic biosensors may be merely based on Prussian blue (PB), which can serve as an efficient electron-transfer mediator with a low redox potential of approximately 0 Volts. However, PB-based biosensors suffer from poor stability during long-term use in biofluids because PB can degrade in neutral and alkaline solutions as the hydroxide ions ($OH^-$), a product of $H_2O_2$ reduction, can break the Fe—(CN)—Fe bond.

To stabilize PB while retaining its catalytic activity, the present disclosure may protect the PB transduction layer with a PB-analogue nickel hexacyanoferrate (NiHCF) protection layer with a similar zeolitic crystal structure that may be catalytically inactive but can form a stabilized solid solution composite, protecting the PB sensor interface. Additionally, an enzyme layer may be protected in a glutaraldehyde-crosslinked bovine serum albumin (BSA) matrix.

Various embodiments of the present disclosure respond to issues described herein. Various embodiments may include a consolidated artificial-intelligence-reinforced electronic skin (CARES) with robust long-term sensing capabilities for stress response monitoring or stress assessment. CARES (also referred to as the wearable assessment system) may be fabricated using a scalable inkjet-printing approach, the wearable assessment system may be capable of multiplexed, non-invasive monitoring of stress-related physiological signals (e.g., pulse waveform, GSR, skin temperature, etc.), sweat metabolites (e.g., glucose, lactate, UA, etc.) and electrolytes (e.g., $NA^+$, $K^+$, $NH_4^+$, etc.) during daily activities. Through the integration of a miniaturized iontophoresis (IP) module into a sweat sensor patch (and/or in a microfluidic sweat sampling component), sweat can be induced autonomously at rest without the need for vigorous exercise.

To realize the practical molecular biomarker monitoring without the need for vigorous exercise, miniaturized IP electrodes coated with carbachol hydrogels may be incorporated into the wearable assessment system for autonomous local sweat induction. Sweat can be continuously secreted from the surrounding glands over a prolonged period of time because of the nicotinic effects of carbachol (for example, transdermally delivered for approximately 5 minutes by means of an approximately 50 microamp current). Efficient sampling may be obtained through microfluidics collection for real-time (or near-real-time) bio-analysis with a higher temporal resolution (higher as compared to conventional systems).

Embodiments of the present disclosure may use highly stable and sensitive electrochemical biosensors, which may use analogous composite materials for stabilizing and conserving sensor interfaces. The resulting biochemical sensors may offer long-term stability of up to or more than 100 hours of continuous operation with minimal signal drifts (potentially seeing amperometric signals decaying less than 0.07% per hour and potentiometric signals draft less than 0.04 mV per hour).

Embodiments of the present disclosure may be built on an ultrathin flexible polyimide (PI) substrate (approximately 4 micrometers) for flexibility and robustness, as well as integrated with microfluidics, the wearable assessment system may conformally laminate on a user's skin (at, for example, a human patient's wrist) for reliable and robust sensing. This may allow for longer periods (e.g., 12-36 hours) of continuous monitoring of daily activities, yielding greater insight into how these signals may vary throughout the day. Embodiments may incorporate machine learning (ML) pipelines or models (discussed below), allowing for previously inaccessible multimodal data to be incorporated into the stress assessments. In other words, the physicochemical sensor data obtained by the wearable assessment system can be used to classify responses to stressors and predict state anxiety levels (a key psychological response to stress) with higher reliability and accuracy.

Due to the ultrathin flexible PI substrate and strong interfacial strength enabled by medical adhesive, embodiments of the present disclosure may make more skin contact than conventional systems. Further, the mechanical resilience against undesirable physical deformations during continuous operations is reduced due to this structure.

Embodiments of the wearable assessment system may include a sensor patch with multiple layers and a skin-interfaced laser engraved microfluidic module. The sensor patch may include carbachol hydrogel-loaded sweat-stimulation electrodes, various enzymatic biosensors (e.g., three enzymatic biosensors), various ion-selective sensors (ISEs) (e.g., three ISEs), a capacitive pulse sensor, a resistive GSR sensor, and/or a skin temperature sensor. The sweat sensor patch may be adapted to adhere to the skin of a human patient by including a skin adhesive, such as medical tape for example, on a lower side of the sweat sensor patch. The sweat sensor patch may also be adapted to induce sweat production from the human patient's skin by dispensing the stimulating agent onto the human patient's skin via the sweat-stimulation electrode. Other embodiments of the wearable assessment system may include more sensors, while further embodiments may include fewer sensors.

Embodiments of the wearable assessment system may include a metabolite detection logical circuit, an electrolyte detection logical circuit, and/or a physiological indicator logical circuit. Said logical circuits may include the biosensors used to measure the concentrations of the relevant biomarkers (or monitor vital signs) and output information representative of said biomarkers in a machine-readable format (e.g., biomarker data).

Embodiments of the wearable assessment system may further include a smart device with one or more processors with machine-readable instruction embedded therein. The machine-readable instructions may cause the one or more processors to analyze the detected metabolite concentrations (detected via the enzymatic biosensors), the detected electrolyte concentrations (detected via the ISEs), and the identified physiological signs (monitored via physiological biosensors or indicators). The machine-readable instructions may further cause the smart device to display an assessment of the human patient's stress response (who is wearing the wearable assessment system) on a graphical user interface. The smart device, as discussed below, may be in wired communication with the wearable assessment system or in wireless communication with the wearable assessment system.

Furthermore, due to the low-cost and mass-producibility of the wearable assessment system, said system may be disposable after each use: where a use for each system may be up to 48 hours, and where users may easily replace the system without the assistance of a medical professional.

Additionally, the wearable assessment system may be shaped in a novel way, configured to adhere comfortably to the wrist of a human patient. The wearable assessment system may be uniquely shaped in the form of a two-dimensional "mushroom." The wearable assessment system, and its individual layers of the multi-layer patch, may include a broad, circular top portion representing the cap of the "mushroom," providing ample surface area for housing various electronic and physical components, including the biosensors, electrodes, stimulating agents (which follow a quarter circle shape nearly along the outside portion of the broad circular top portion), and inlets (among other features). Extending downward from the center of the cap, is a narrower (narrower in relation to the edges of the cap), rectangular section resembling the stem of the "mushroom," which may serve as a conduit for wiring and connectivity interfaces (e.g., pins), configured for integration with external devices. The overall design not only increases the functional area for sensor and stimulating agent placement, but also facilitates ergonomic attachment to the skin, ensuring comfort and stability during use. Such design can be observed in FIGS. 1A-1B.

Turning now to the figures. FIG. 1A is an example diagram showing a wearable assessment system 100, in accordance with various embodiments of the disclosed technology. In other words, FIG. 1A depicts an example diagram of a wearable assessment system 100 schematic including vital sign monitoring 101-103, sweat stimulation and sampling 104, and key electrolyte 105A-105C and metabolite 106A-106C detection.

The wearable assessment system 100 may include various sensors that may be configured to monitor vital signs of a patient. As discussed throughout this disclosure, in addition to chemical sensors, embodiments of the wearable assessment system 100 may also include various physical sensors that can monitor stress-related vital signs. These sensors may be configured in a physiological indicator logical circuit.

In embodiments, the wearable assessment system 100 may include a temperature sensor 101. The temperature sensor 101 may measure the skin temperature of a patient in an area adjacent or nearly adjacent to the location of the temperature sensor 101 as configured within the wearable assessment system 100. The temperature sensor 101, for example, may be a printed resistive temperature sensor 101 integrated into embodiments of the wearable assessment system 100 that may be used to measure skin temperature in situ with sensitivities at approximately 0.115% degrees Celsius$^{-1}$ (+/−0.1%) in physiological temperature ranges between 25 and 50 degrees Celsius. Considering that temperature may have a strong influence on enzymatic activities, the temperature information may be used to calibrate the response of the enzymatic biosensors (e.g., the metabolite sensors 106A-106C) to achieve higher levels of accuracy in situ metabolic analysis. Additionally, environmental factors, such as humidity, have minimal influence on the performance of the chemical sensors, but can be accounted for partially via the temperature sensor 101. Humidity may have minimal influence due to the impermeable (or nearly impermeable) PI packaging of the sweat sensor patch.

The wearable assessment system 100 may further include a GSR sensor 102, for purposes in accordance with the principles discussed herein. Embodiments of the wearable assessment system 100 may use printed Ag electrodes as the GSR sensor 102, which may be more conductive than commercial gel electrodes.

Further, the wearable assessment system 100 may include a pulse waveform sensor 103 that may be configured to measure cardiac functions of a patient, including pulse, in accordance with various principles as discussed herein. For example, pulse waveform sensor 103 may be a capacitive pressure sensors placed approximately above a user's radial artery to measure pulse waveform. Due to the soft PDMS-engraved airgap (e.g., 214 of FIG. 2A, discussed below), this type of pressure sensor may be highly sensitive to soft pressure loads (such as a feather), with sensitives of 113.1% kPa$^{-1}$ (+/−10%) in the range of 0 to 500 Pa.

The wearable assessment system 100 may include a sweat stimulation electrode 104A, 104B. There may be a sweat stimulation electrode 104A, 104B on either side of the wearable assessment system 100. For example, as depicted in FIG. 1A, the left side of the patch may include a first set of sweat stimulation electrodes 104A and the right side of the patch may include a second set of sweat stimulation electrodes 104B. The sweat stimulation electrodes 104A, 104B may each include an iontophoresis cathode and anode. The iontophoresis anode may include carbachol or hydrogel that may stimulate sweat production when applied the skin of a human. In some embodiments, there may only be one sweat stimulation electrode, while in other embodiments there may be more than two sweat stimulation electrodes. The sweat stimulation electrodes 104A, 104B may wrap approximately around the outer edge of the cap of the wearable assessment system 100, such the electrodes are not touching the edge of the cap.

In embodiments, the sweat stimulation electrode 104A, 104B may be controlled by a control module or logical circuit (not shown). The control module may be integrated into the smart device (as discussed below) or may be an independent processing unit. The control module may allow a user to implement electrostimulation using the sweat stimulation electrodes 104A, 104B to induce the flow of sweat. The electrostimulation may trigger sweat stimulating agents that may also further trigger the flow of sweat. The sweat stimulating agents may coat the sweat stimulating electrodes. The control module may also allow a user to implement a release of a stimulating agent (e.g., carbachol or similar) to continue inducing sweat flow. The control module may allow a user to set a duration for the induction of sweat over a period of time or at increments in time.

The wearable assessment system 100 may include electrolyte detection logical circuit with electrolyte sensors 105A-105C. The electrolyte sensors 105A-105C may be ISEs, as discussed throughout this disclosure. The electrolyte sensors 105A-105C may measure electrolyte concentrations in a sweat sample, which may be produced by the sweat stimulation electrodes 104A, 104B or by natural sweat production (for example, during exercise). For example, the wearable assessment system 100 may include a sodium (e.g., $NA^+$) sensor 105A, an ammonium (e.g., $NH_4^+$) sensor 105B, and/or a potassium (e.g., $K^+$) sensor 105C. Each sensor may measure a given concentration of each electrolyte and output a data value representative of said concentration of each electrolyte. The wearable assessment system 100 may also include other electrolyte sensors (or ISEs) or different combinations of the discussed sensors.

The wearable assessment system 100 may include metabolite sensors 106A-106C. The metabolite sensors 106A-106C may be enzymatic biosensors, as discussed throughout this disclosure. The metabolite sensors 106A-106C may measure metabolite concentrations in a sweat sample, which may be produced by the sweat stimulation electrodes 104A, 104B or by natural sweat production (for example, during exercise). For example, the wearable assessment system 100 may include a lactate sensor 106A, a glucose sensor 106B, and/or a UA sensor 106C. Each sensor may measure a given concentration of each metabolite and output a data value representative of said concentration of each metabolite. The wearable assessment system 100 may also include other metabolite sensors (or enzymatic biosensors) or different combinations of the discussed sensors.

Additionally, the wearable assessment system 100 preparation approach described herein may not be limited to the six sensors discussed throughout this disclosure. Rather, such principles can serve as a universal and readily reconfigurable method for other enzymatic and ionophore-based biosensors towards a broad range of practical applications (e.g., medical monitoring, dietary monitoring, etc.).

Figure 1B:
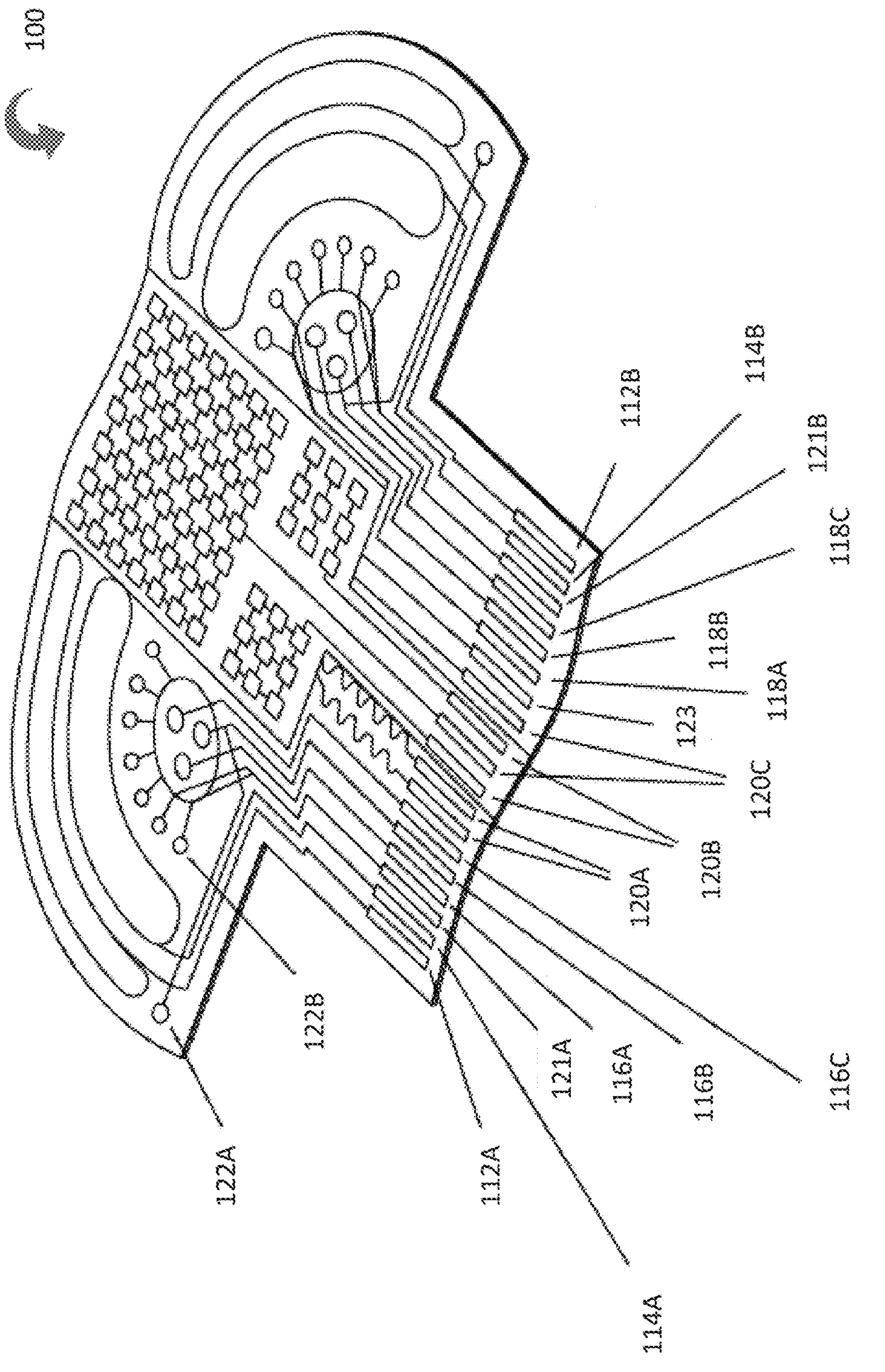

FIG. 1B is an example of a wearable assessment system 100 including a pin diagram, in accordance with various embodiments of the disclosed technology. The wearable assessment system 100 may include various pins that may allow for the system 100 to be connected or placed in wired or wireless communication with a smart device or computing device (not shown).

The wearable assessment system 100 may include pins for the sweat stimulation electrodes 104A, 104B of FIG. 1. These pins may include an iontophoresis cathode pin 112A, 112B, and iontophoresis anode pin 114A, 114B, which may be on corresponding sides of the wearable assessment system 100 as their respective sweat stimulation electrodes 104A, 104B. For example, the cathode of sweat stimulation electrode 104A may connect to iontophoresis cathode pin 112A, whereas the anode of sweat stimulation electrode 104A may connect to iontophoresis anode pin 114A. Similarly, the cathode of sweat stimulation electrode 104B may connect to iontophoresis cathode pin 112B, whereas the anode of sweat stimulation electrode 104B may connect to iontophoresis anode pin 114B.

The wearable assessment system 100 may include pins for the electrolyte sensors 105A-105C of FIG. 1. These pins may be part of the electrolyte detection logical circuit. These pins may include a sodium sensor pin 116A, an ammonium sensor pin 116B, and/or a potassium sensor pin 116C. FIG. 1B depicts the electrolyte sensors 105A-105C and the electrolyte sensor pins 116A-116C on the left side of the wearable assessment system 100, however, other configurations may be possible, for example, placing the electrolyte sensors 105A-105C and the electrolyte sensor pins 116A-116C on the right side or center of the wearable assessment system 100.

The wearable assessment system 100 may include pins for the metabolite sensors 106A-106C of FIG. 1. These pins may be part of the metabolite detection logical circuit. These pins may include a glucose sensor pin 118A, a lactate sensor pin 118B, and/or a UA sensor pin 118C. FIG. 1B depicts the metabolite sensors 106A-106C and the metabolite sensor pins 118A-118C on the right side of the wearable assessment system 100, however, other configurations may be possible, for example, placing the metabolite sensors 106A-106C and the electrolyte sensor pins 118A-118C on the left side or center of the wearable assessment system 100.

The wearable assessment system 100 may include pins for the vital sign monitoring sensors 101-103 of FIG. 1. These pins may be part of the physiological indicator logical circuit. These pins may include a skin temperature sensor pin 120A, a GSR sensor pin 120B, and/or a pulse sensor pin 120C.

The wearable assessment system 100 may include one or more reference electrodes (RE) 121A, 121B and a counter electrode (CE) 123 for the metabolite and/or electrolyte sensors. These pins may be included in the metabolite and/or electrolyte detection logical circuits. The references electrodes 121A, 121B may be an electrode with a stable and known electrode potential. The counter electrode (which may also be referred to as an auxiliary electrode) may be an electrode used in, for example, a three-electrode electrochemical cell for voltammetric analysis or for other reasons in accordance with the disclosures discussed herein.

The wearable assessment system 100 may include sweat inlets 122A, 122B as part of the microfluidic sweat sampling component that may open to allow sweat (that may or may not have been stimulated by the carbachol or hydrogel alone or in combination with the sweat stimulation electrodes 104A, 104B) to be collected by the wearable assessment system 100. There may be multiple inlets that contact or nearly contact the human patient's skin. The microfluidic sweat sampling component, including the sweat inlets 122A, 122B may be coupled to the sweat sensor patch (the sweat sensor patch generally referring to the various combinations of biosensors disposed on the wearable assessment system). The collected sweat sample may be analyzed by the electrolyte sensors 105A-105C and/or the metabolite sensors 106A-106C to determine concentrations of measured electrolytes and metabolites present in the sweat sample. The inlets 122A, 122B may allow for optimized microfluidic sweat collection to achieve more rapid refreshing time between samples. Several parameters may be selected for optimization including, for example, the placement of the inlets 122A, 122B relative to each other, the number of inlets 122A, 122B, the orientation of the inlet channels 122A, 122B, the distance between the inlets 122A, 122B, the distance between each inlet and the electrolyte 105A-105C or metabolite sensors 106A-106C, and other factors.

As discussed, the wearable assessment system 100 may include a plurality of inlets 122A, 122B. The wearable assessment system 100 may also include a microfluidic channel layer 226 (as discussed in relation to FIG. 2B) that may allow for sweat to be channeled from the inlets 122A, 122B to the electrolyte 105A-105C and/or metabolite sensors 106A-106C. The inlets 122A, 122B may be configured relative to each other and the electrolyte 105A-105C and/or metabolite sensors 106A-106C at a selected angular span, and may also be positioned to have a selected flow direction relative to said sensors. As depicted, for example, in FIG. 1B, the number of inlets 122A, 122B may be eight on each side of the wearable assessment system 100, for a total number of inlets 122A, 122B being sixteen. In other embodiments, there may be more or less than sixteen inlets 122A, 122B, with more or less than eight inlets 122A, 122B being on each side of the wearable assessment system 100. Some embodiments may have more inlets 122A, 122B on one side of the wearable assessment system 100, which may account for sensors that require higher amounts of sweat for analysis.

Figure 2A:
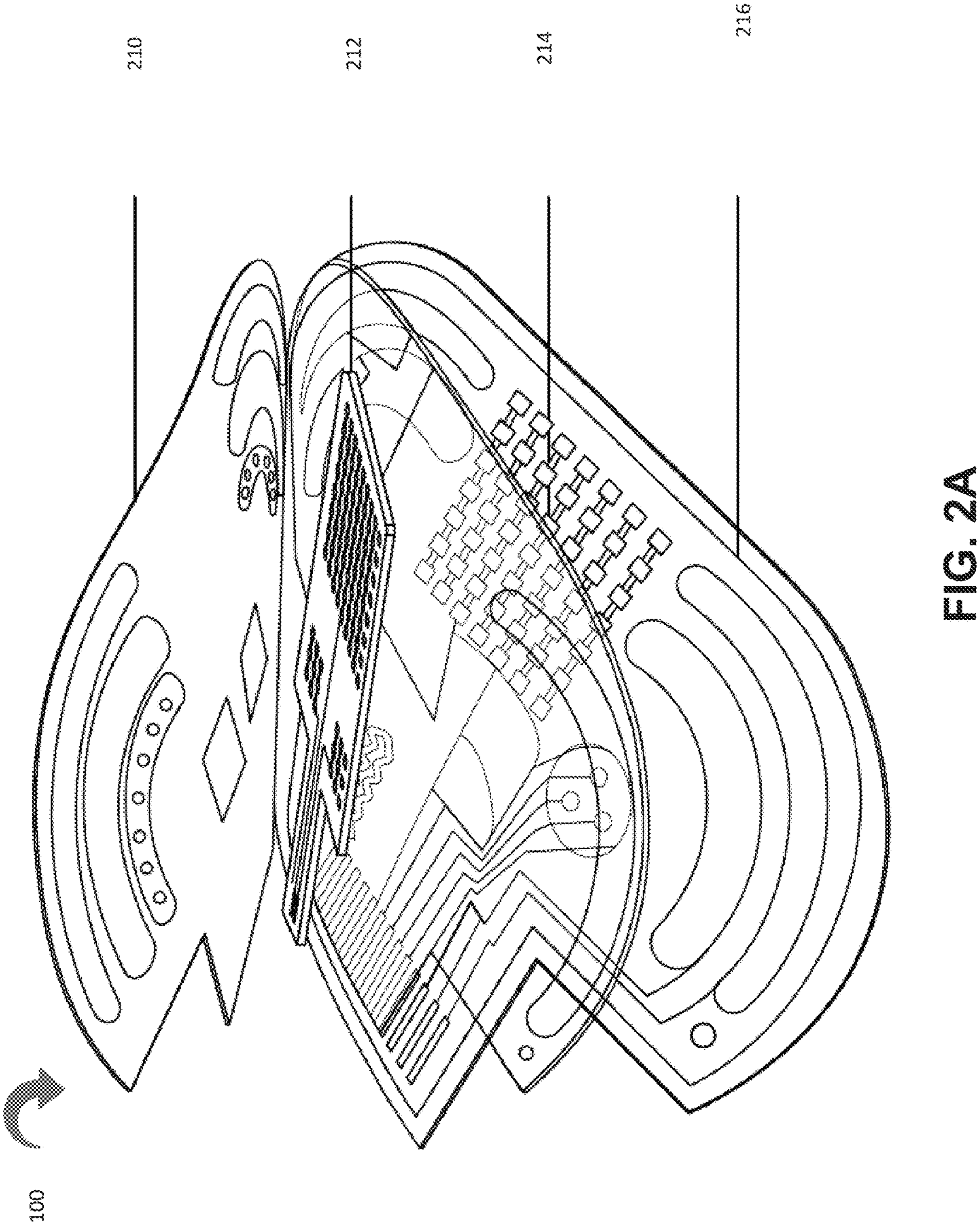
FIGS. 2A-2B are example diagrams showing an exploded illustration of a wearable assessment system, in accordance with various embodiments of the disclosed technology.

FIG. 2A is an example diagram showing an exploded illustration of a wearable assessment system 100, in accordance with various embodiments of the disclosed technology. In other words, FIG. 2A depicts an example exploded diagram of a wearable assessment system 100 schematic showing the layered structure that assembles a sweat microfluidics layer 210 (also referred to as the microfluidic sweat sampling component), an electrode 212, a PDMS air gap 214, and a sensor patch 216.

The wearable assessment system 100 may include various layers. The layers may be placed in different orders than depicted in FIG. 2A. In some embodiments, the sweat microfluidics layer 210 may be placed on top of the electrode 212, such that portions of the electrode 212 may pass through openings of the sweat microfluidics layer 210 and come into contact with the human patient's skin when the wearable assessment system 100 is worn by a human patient. A portion of, or the entirety of, one side of the sweat microfluidics layer 210 may be in contact with the skin of a human subject. The sweat microfluidics layer 210 may include inlets. The sweat microfluidics layer 210 may further include hydrogel or carbachol, which may stimulate sweat production. The hydrogel may be disposed on the sweat microfluidics layer 210 around a quarter-circle on either upper portion of the wearable assessment system 100 (as depicted in FIGS. 1A-2B). The electrode 212 may be disposed between the sweat microfluidics layer 210 and the PDMS air gap 214. The PDMS air gap 214 may be disposed between the electrode 212 and the sensor patch 216. The PDMS air gap 214 may provide for channels that allow the collected sweat sample to be channeled from the inlets on the sweat microfluidics layer 210 into the sensors on the sensor patch 216. The sensor patch 216 may include various sensors (as discussed in relation to FIG. 1A) and may have sweat channeled from the inlets on the sweat microfluidics layer 210 via the PDMS air gap 214 and into the sensors on the sensor patch 216.

Figure 2B:
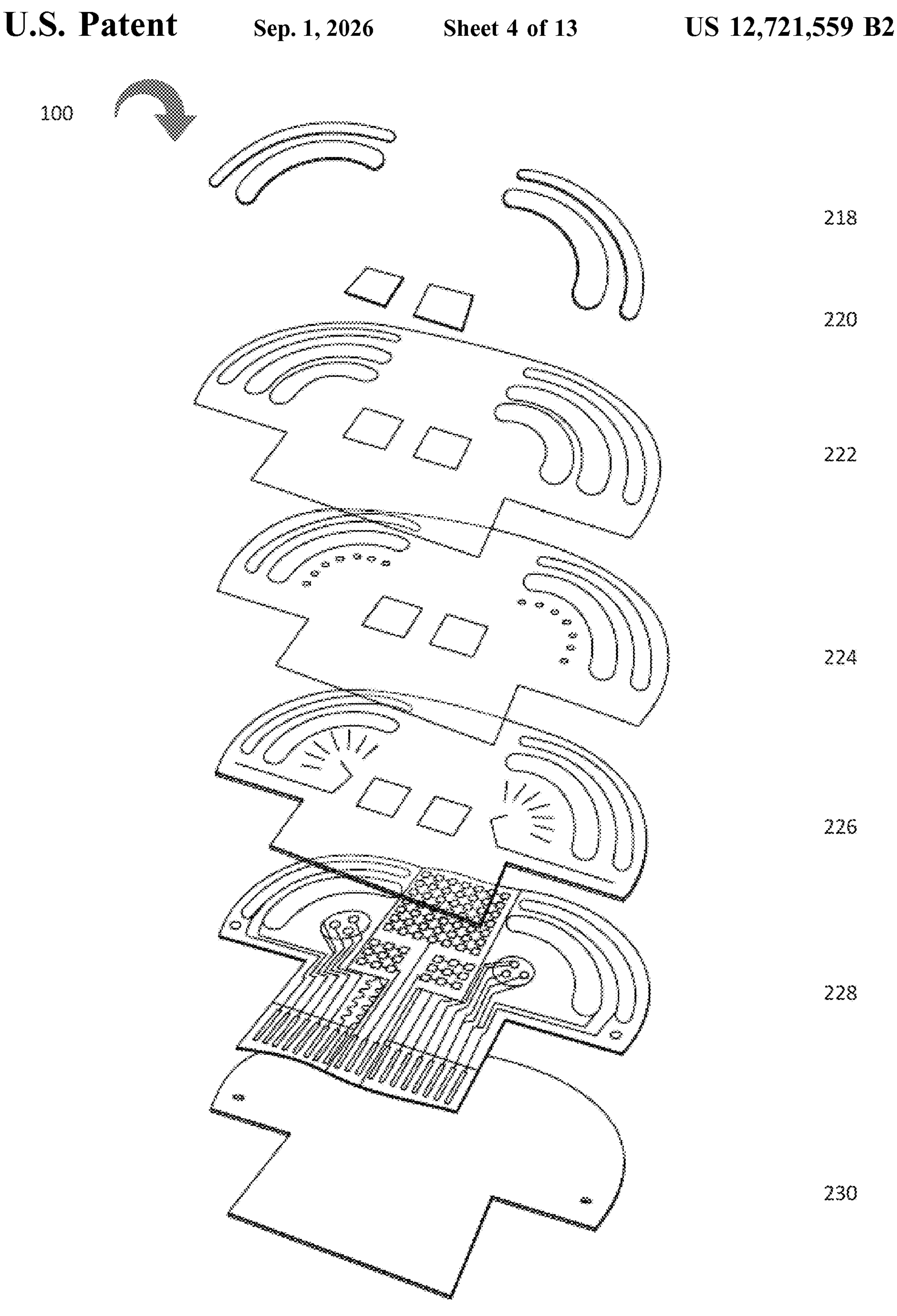

FIG. 2B is an example diagram showing an exploded illustration of a wearable assessment system 100, in accordance with various embodiments of the disclosed technology. In other words, FIG. 2B depicts an example exploded diagram showing a layer breakdown of the wearable assessment system 100.

The wearable assessment system 100 may include a carbachol or hydrogel layer 218, a gel or polyimide (sweat-stimulation) electrode layer 220, a skin adhesion (or M-tape) layer 222, a sweat inlet (or PET) layer 224, a microfluidic channel (or first PDMS) layer 226, a sensor patch layer 228, and an encapsulation (or second PDMS) layer 230.

The carbachol gel layer 218 may be used for sweat induction as it can enable a long-lasting sudomotor axon reflex sweat secretion from the surrounding sweat glands (due to its nicotinic effects).

The wearable assessment system 100 may include layers of double-sided and/or single-sided medical adhesives 222. The system 100 may include a sweat-stimulation electrode 220. The layers of the wearable assessment system 100 may be patterned with channels, inlets, hydrogel outlines, and reservoirs. Hydrogel outlines may be patterned to enable a flow of current from the top of the sweat-stimulation electrode 220 to deliver sweat induction agents (e.g., carbachol, hydrogel, etc.) from the hydrogel layer 218 to the skin. The wearable assessment system 100 may further include a skin adhesion layer 222 that may be in direct contact with a skin area of a user, and may further include openings for the sweat-stimulation electrode 220 and the hydrogel layer 218. The adhesive layer 222 in combination with the hydrogel layer 218 may be patterned with an accumulation well to collect stimulated sweat. The wearable assessment system 100 may also include a sweat inlet layer 224 in contact with the adhesive layer 222 and the hydrogel layer 218. The inlet layer 224 may include a single or plurality of sweat inlets (e.g., sweat inlets 122A, 122B of FIG. 1B) that have sweat channeled thereto from the accumulation well(s) of the adhesive layer 222. The wearable assessment system 100 may also include a microfluidic channel layer 226 patterned with a plurality of microfluidic channels. The microfluidic channel layer 226 may be in direct contact with the inlet layer 224 and may be part of the microfluidic sweat sampling component. Sweat collected in accumulation wells may flow to the inlets on the inlet layer 224 and then in turn flow through the channels of the microfluidic channel layer 226. In some embodiments, the wearable assessment system 100 may further include a reservoir layer (not shown), which may be patterned with a reservoir and an outlet. Sweat may flow the microfluidic channel layer 226 into the reservoir. After sampling, sweat may flow through the outlet. The reservoir layer may lie between the microfluidic channel layer 226 and the polyimide electrode layer 220.

The wearable assessment system 100 may further include a sensor patch layer 228, which may include the various electrolyte sensors (e.g., 105A-105C), metabolite sensors (e.g., 106A-106C), and physiological sensors or indicators (e.g., 101-103) described in relation to FIGS. 1A-1B. The wearable assessment system 100 may further include an encapsulation layer 230 that may protect the sensor patch layer 228 from biofluids that can reduce the efficacy and longevity of the sensors in the sensor patch layer 228.

Figure 3A:
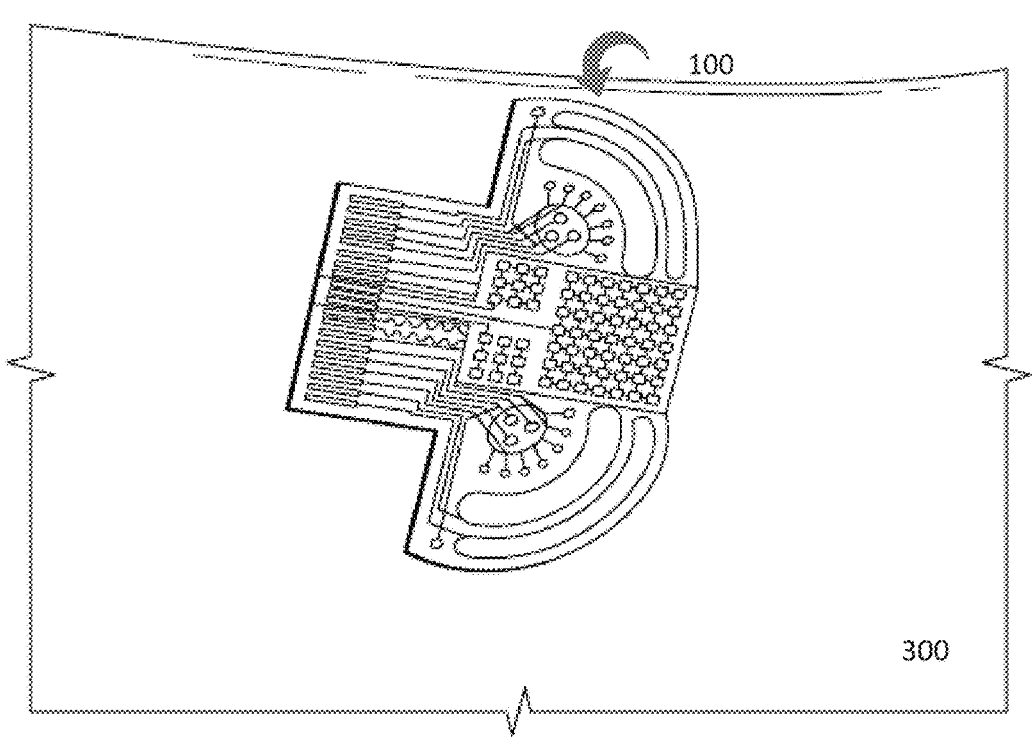
FIGS. 3A-3B are example diagrams a wearable assessment system attached to the skin of a human subject, in accordance with various embodiments of the disclosed technology.
Figure 3B:
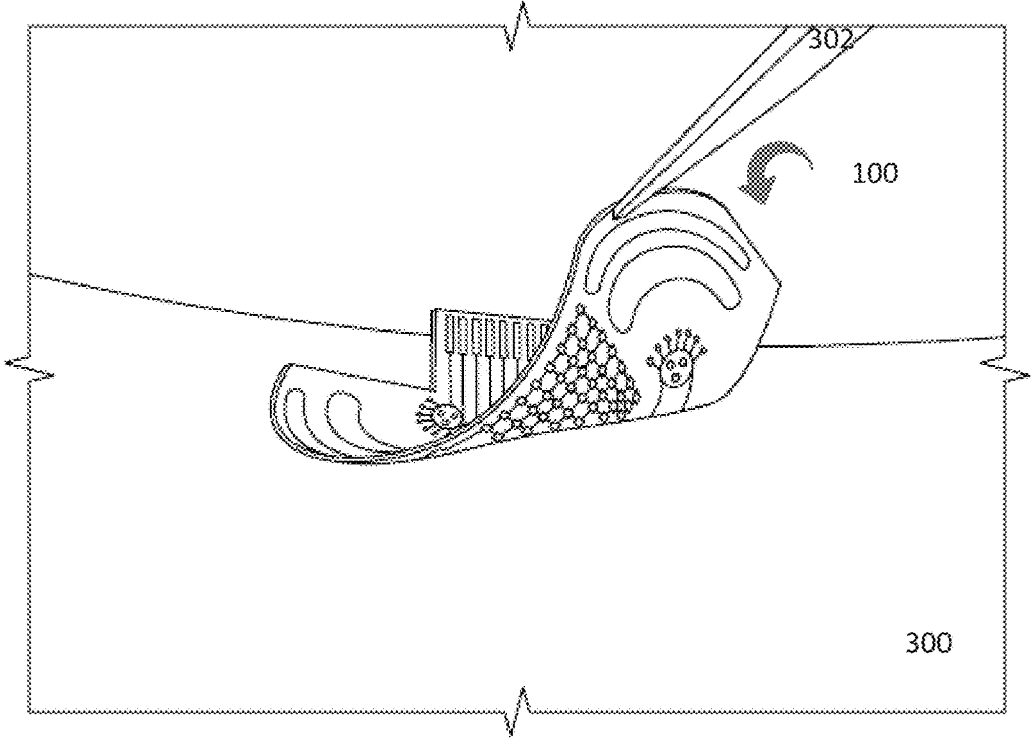

FIGS. 3A-3B are example diagrams showing a wearable assessment system 100 attached to the skin 300 of a human patient, in accordance with various embodiments of the disclosed technology. In other words, FIGS. 3A-3B depict an example wearable assessment system 100 secured to the skin 300 of a patient (FIG. 3A) and being comfortably removed with forceps 302 from the skin 300 of patient (FIG. 3B) due to the flexible nature of the system. The wearable assessment system 100 may be constructed on an ultrathin flexible polyimide (PI) substrate (for example, with a thickness of approximately 4 micrometers+/−1 micrometer) for flexibility and robustness. Additionally, embodiments of the present disclosure may be secured to the skin 300 of a human subject on or around the wrist of the patient, and as such may benefit from being flexible due to the curved nature of the typical human wrist.

Figure 4A:
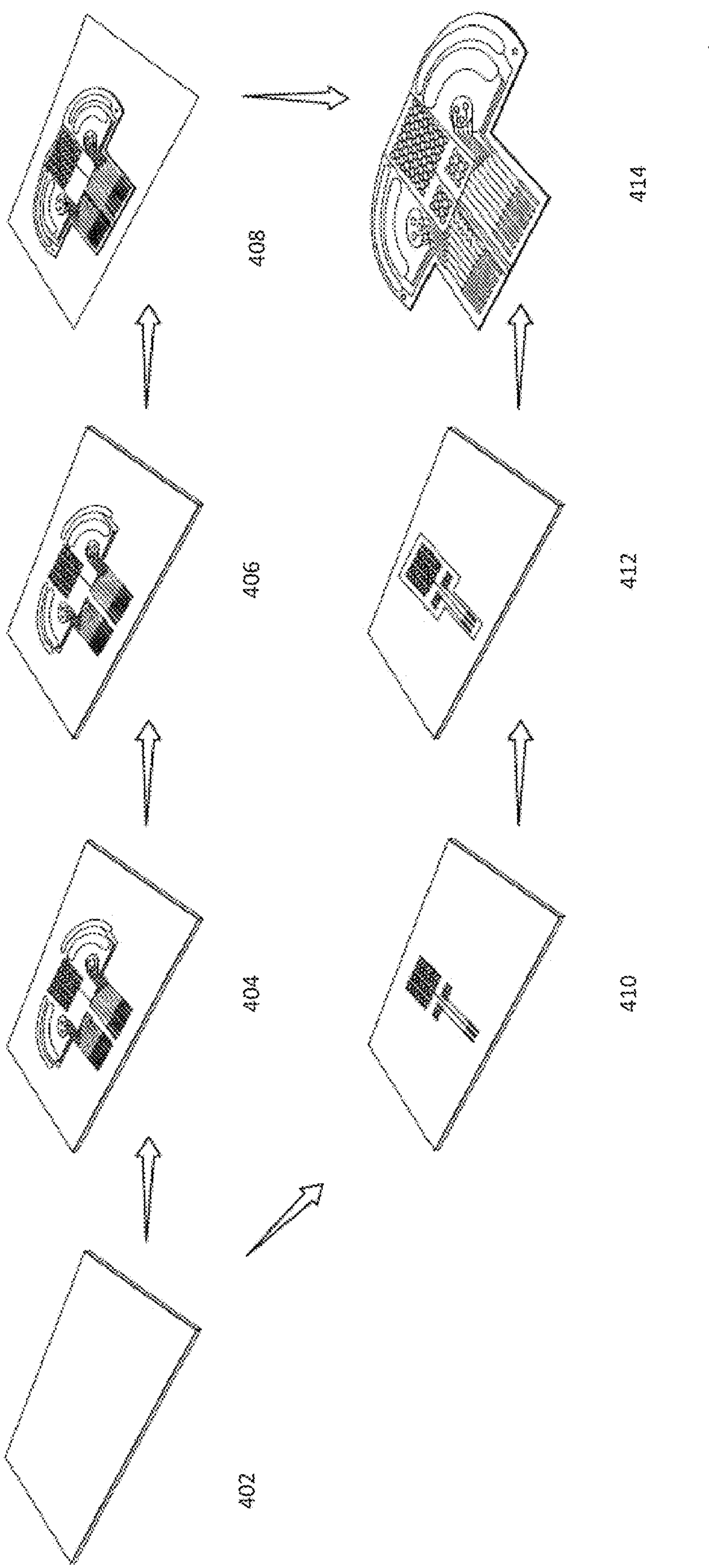
FIG. 4A is a flow diagram showing an example fabrication process of a wearable assessment system, in accordance with various embodiments of the disclosed technology.

FIG. 4A is a flow diagram showing an example fabrication process of a wearable assessment system 100, in accordance with various embodiments of the disclosed technology. The example fabrication process may include PI coating a $SIO_2$ wafer 402, inkjet printing a bottom layer 404, PDMS spin-coating the bottom layer 406, laser patterning and etching 408 the bottom layer, inkjet printing a top layer 410, laser patterning the top layer 412, and pattern transfer and assembly of the top and bottom layer 414.

In various embodiments, the wearable assessment system 100 may be mass-fabricated through serial inkjet printing (as discussed in relation to FIG. 4B) of silver and carbon, or other suitable materials, as the interconnects and electrodes for the top and bottom layers. In some embodiments, a middle polydimethylsiloxane (PDMS)-based airgap layer (e.g., microfluidic channel layer 226 of FIG. 2B) may be spin-coated between the top and bottom layers, as the soft PDMS may facilitate pulse pressure sensitivity and sweat reservoir collection and channeling. The microfluidic component may be assembled in a sandwiched structure (e.g., PDMS/polyethylene terephthalate/medical tape) (see FIGS. 2A-2B) and may include two separate reservoirs that can enable fresh sweat sampling and rapid refreshing for more accurate sweat analysis with higher temporal resolution.

Figures 4B, 4C:
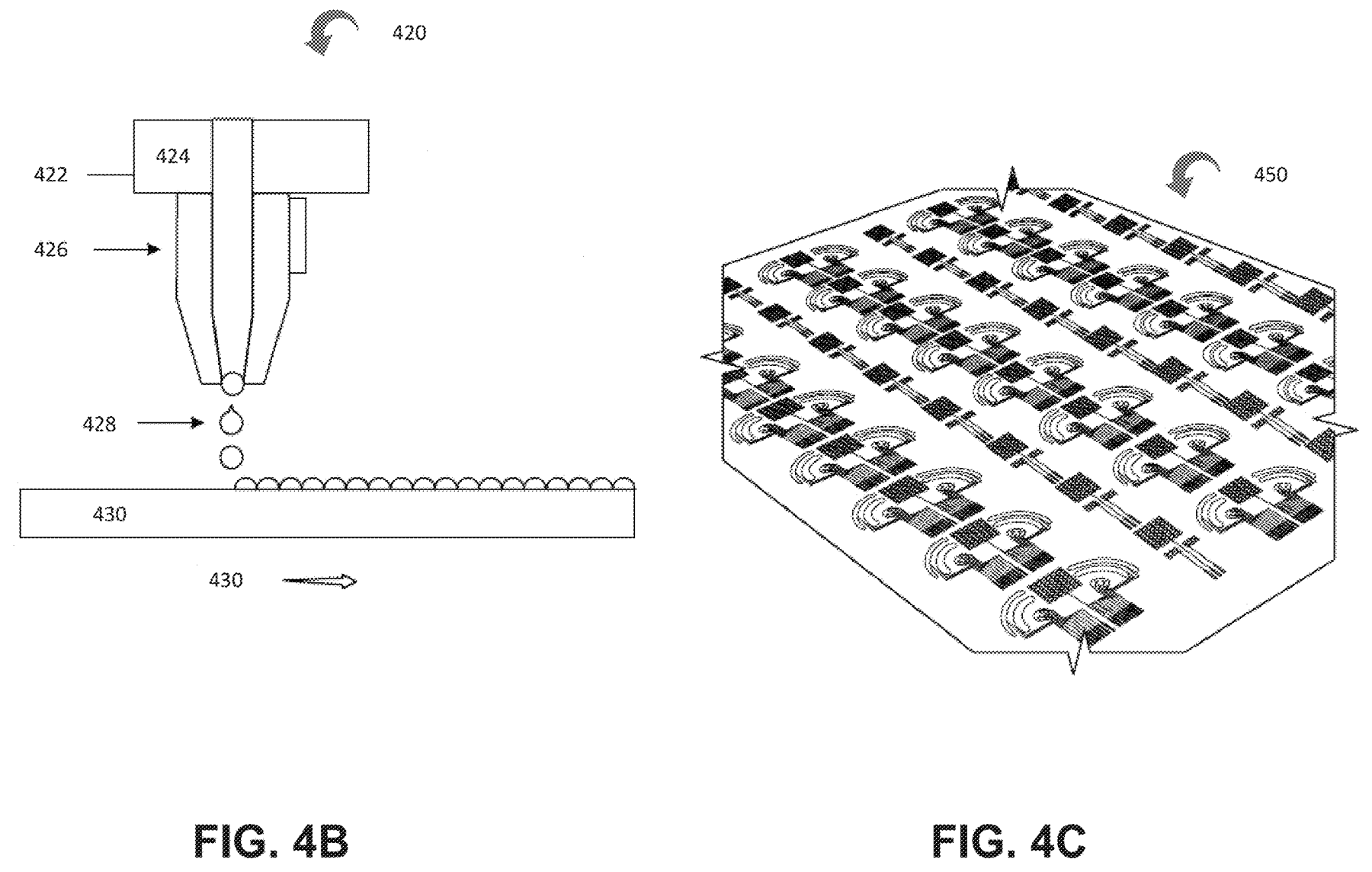

FIG. 4B is an example diagram showing the schematics of an example inkjet printing mechanism 420, in accordance with various embodiments of the disclosed technology. The inkjet printing mechanism 420 may store ink 422 in a reservoir 424, which can be deposited via droplets 428 produced by a nozzle 426. The droplets 428 may be deposited (or in some embodiments, electrodeposited) on a substrate 430, which may be moved (i.e., substrate motion 432) to allow for the nozzle 426 to remain stationary during printing.

The inkjet printing mechanism 420 may be used to fabricate enzymatic sensors, for example, electrolyte 105A-105C and/or metabolite sensors 106A-106C, as described herein. The inkjet printing mechanism 420 may electrodeposit gold nanoparticles (or similarly structured nanoparticles) onto an inkjet-printed inert carbon electrode to provide a high electroactive area for more sensitive electrochemical sensing followed by PB—NiHCF deposition. Scanning transmission electron microscopy (STEM) and energy dispersive spectroscopy (EDS) analyses may indicate that NiHCF can form a thin protective layer on PB with an obscure boundary.

The general material strategy of the wearable assessment system 100 that may be based on electrodes prepared by inkjet printing, as described herein, may be applicable to electrodes manufactured using other scalable technologies, including laser engraving and thin-film evaporation.

FIG. 4C is an example diagram showing an array of wearable assessments systems 450 fabricated via mass-producible and low-cost inkjet printing, in accordance with various embodiments of the disclosed technology.

Figure 5A:
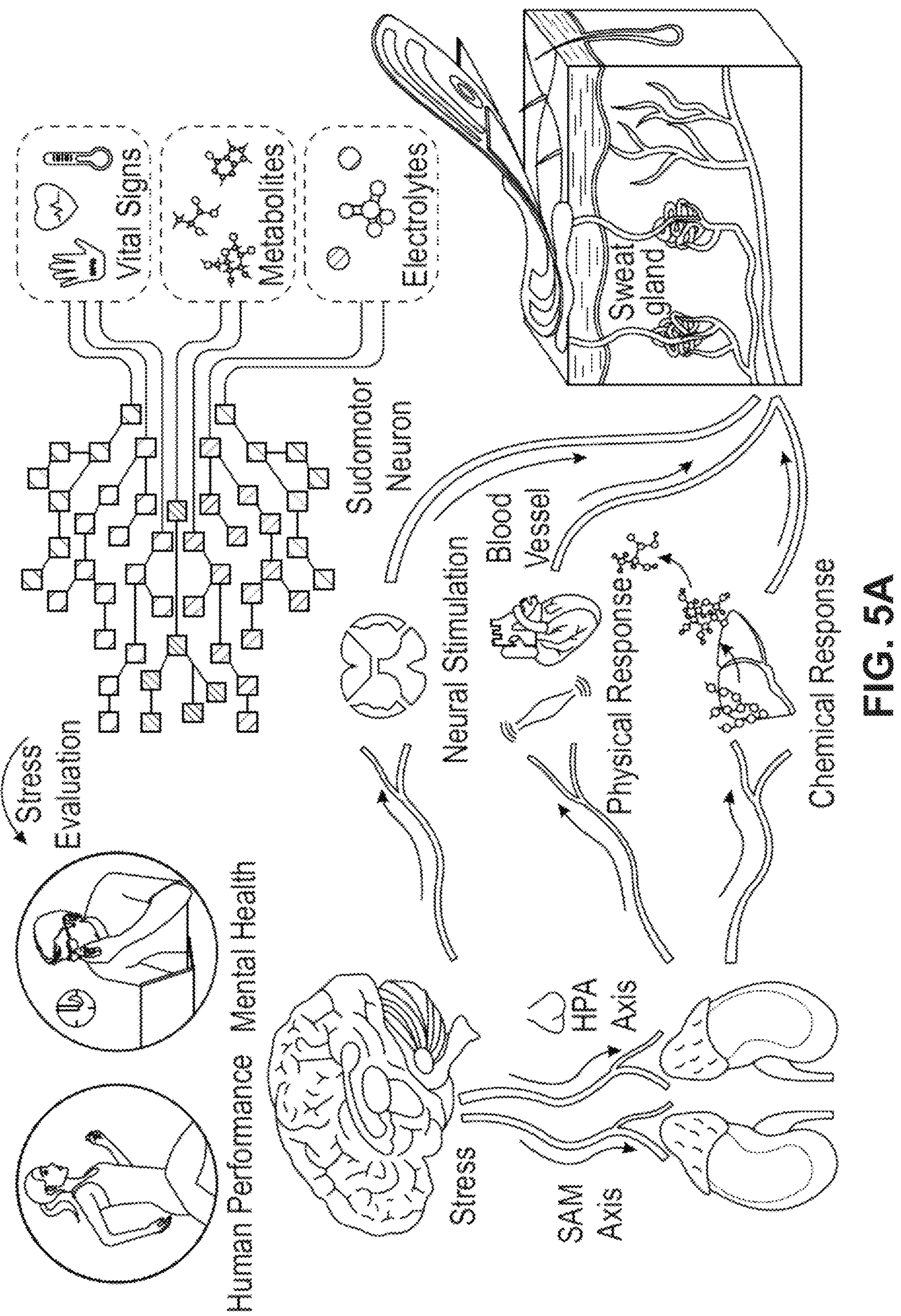
FIG. 5A is an example illustration showing a process a wearable assessment system may perform to continuously monitor multimodal physiological and biochemical responses from skin and perform artificial-intelligence-powered stress assessments, in accordance with various embodiments of the disclosed technology.

FIG. 5A is an example illustration showing a process that a wearable assessment system may perform to continuously monitor multimodal physiological and biochemical responses from skin and perform artificial-intelligence-powered stress assessments, in accordance with various embodiments of the disclosed technology. Processes disclosed by FIG. 5A may be interpreted throughout this disclosure.

Figure 5B:
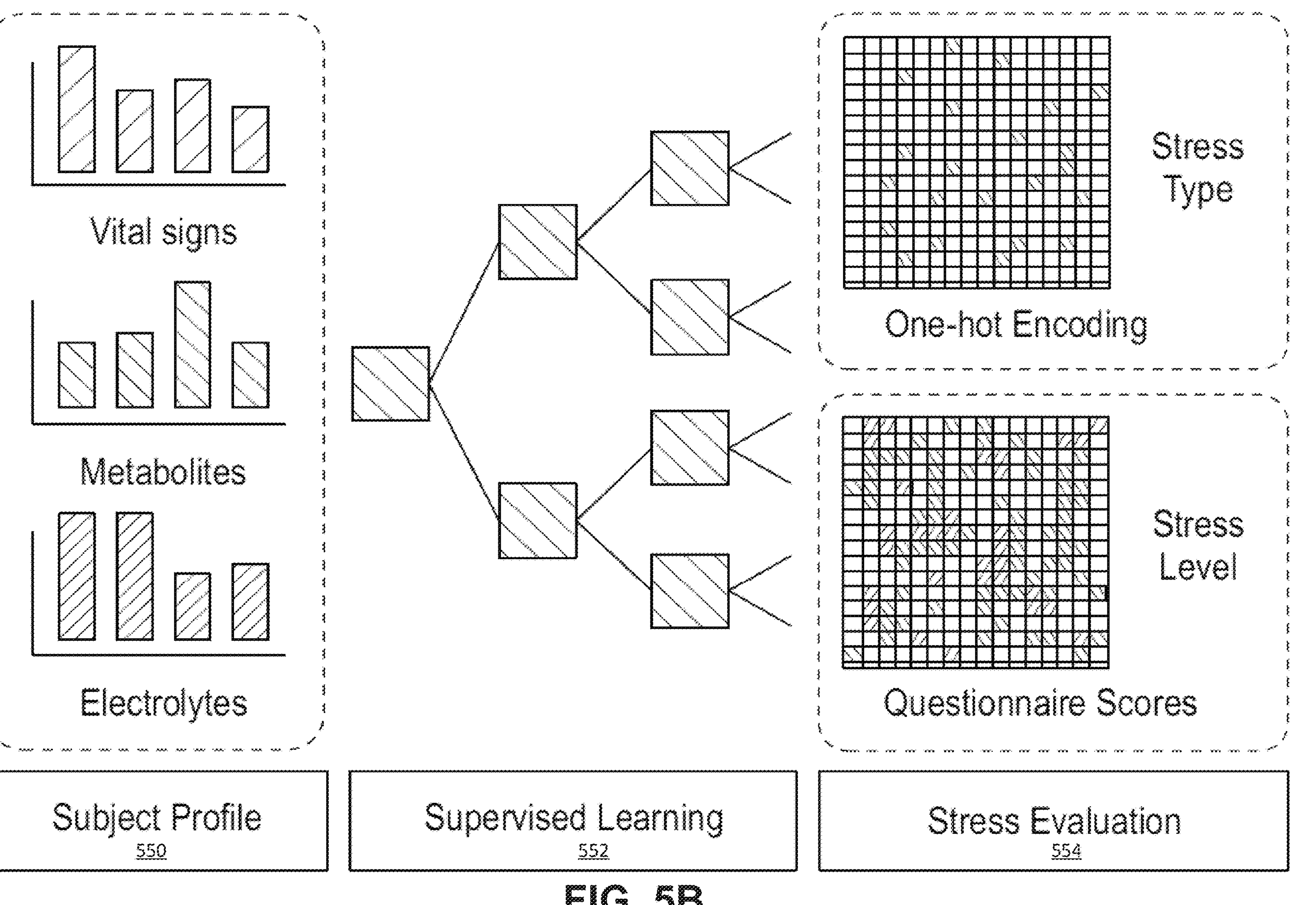
FIG. 5B is an example of a flow diagram showing a machine learning process for a wearable assessment system's stressor classification and stress/anxiety level assessment, in accordance with various embodiments of the disclosed technology.

FIG. 5B is an example of a flow diagram showing a machine learning process for a wearable assessment system's stressor classification and stress/anxiety level assessment, in accordance with various embodiments of the disclosed technology.

The wearable stress assessment system (e.g., the wearable assessment system 100 of FIGS. 1A-4A) may further include a smart device. In some embodiments, the smart device may be a computing device, such as a processor that stores non-transitory machine readable instructions, and may further be connected to the wearable stress assessment system via wired or wireless communication methods, or alternatively, may be integrated into the wearable assessment system for real- or near-real-time processing. The smart device may be configured for wireless communication with a smart device (e.g., a cell phone) or computer. Wireless communication may occur via Wi-Fi, via Bluetooth, or via any other wireless communication methods. The smart device may be configured for wired communication with a mobile device or computer via the various pins (e.g., pins 112A-120C of FIG. 1B) and with the use of any wired communication system. The mobile device may be a smart phone or other wireless device, such as a tablet, equipped with an application. The application may display detected health information, including stress assessments, determined by the wearable assessment system. The application may also be used to analyze, organize, and/or transmit collected health data from the wearable assessment system.

The smart device may be preprogrammed with various steps for determining a stress assessment. The steps may be performed using machine learning or supervised learning 552 methods. The steps may include determining a subject profile 550 from the measured vital signs, metabolite concentrations, and/or electrolytes. Such subject profile 550 may be determined from the data produced by the logical circuits via the measurements taken by the multimodal sensor patch included in the wearable assessment system. The subject profile 550 may be initially trained with a supervised learning model 552 (as discussed below) and subsequently analyzed using an unsupervised machine learning model and/or trained with the supervised learning model 552 to produce stress assessments 554 based on the subject profile 550. The resulting evaluation may be displayed to the user on a graphical user interface in combination with other methods to produce a stress assessment or stress evaluation 554 (as discussed below).

To form the subject profile 550, the smart device may analyze individually, or a combination of, the detected metabolite concentrations, the detected electrolyte concentrations, and/or the monitored vital signs. The individual concentrations and/or monitored vital signs may be used to determine a stress assessment 554, which may be displayed to the user. The stress assessment 554 may be based, wholly or in part, on the analyzed metabolite concentrations, analyzed electrolyte concentrations, and/or monitored vital signs. The wearable stress assessment system may use an unsupervised machine learning model to determine the stress assessment 554, which is in whole or in part based on the supervised learning model 552. The machine learning model may include data streaming, data preprocessing and feature extraction, supervised learning 552, stressor classification, and stress response classification. In some embodiments, the machine learning model may have both the input (e.g., biomarker concentrations and vital signs) and output (e.g., stress assessment 554) known, for example, by comparing input with questionnaires (e.g., in a supervised learning model 552). While in other embodiments, the machine learning model may only have the input known and the output is determined based on the supervised learning model in combination with other unsupervised machine learning methods. Stress assessments 554 may include various types of determinations including stress detection, stressor type, and anxiety level.

The unsupervised machine learning model trained besides the supervised learning model 552 may include data preprocessing and feature extraction. The machine learning methods derived from the supervised learning model 552 may include performing data preprocessing asynchronously to extract features. For example, data preprocessing may include a pulse feature extraction algorithm. Through the pulse feature extraction algorithm, each pulse waveform collected could be analyzed and applied to a floor function to select the closest pulse feature within each time interval. Data preprocessing may also include manually shifting signals from the biomarker sensors (e.g., electrolyte 105A-105C and/or metabolite sensors 106A-106C) by a given time (e.g., approximately 300 seconds) to align with physical signals due to natural sweat delay. Data preprocessing may also include extracting heart rate data in figure plots from the pulse features and smoothing the heart rate data by the moving average (MA) for a period of time (e.g., approximately 100 seconds) to show the trends more clearly. Data preprocessing may include recording the time stamp when each subject expressed stress, and performing manual data labelling. Data preprocessing may include normalizing some or all features with regard to each subject during each stress test, to minimize variations from intrasubject responses and to generalize the model among the population. Data preprocessing may include shuffling the training and testing datasets and dividing them into 8:2, respectively. Data points may be randomly selected using an equal representation of each class.

The machine learning methods derived from the unsupervised learning model may further include validating feature extraction before developing supervised learning models 552 by projecting the multidimensional feature space into 2D space by means of t-distributed stochastic neighbor embedding, where data from stress/relaxation may naturally form distinctive clusters, which can be indicative of the discriminative power of the features.

The machine learning methods derived from the supervised learning model 552 may further include developing machine learning models to link biological and chemical features to stress detection, stress types, and state anxiety levels from questionnaire scores. Training models for developing supervised learning models 552 can be built based on the data collected from various subjects facing different stressors. Signals on the wearable assessment system can be calibrated and normalized to ensure that the features extracted after data preprocessing were stable against patch variations and moderate motion artifacts during the training. The supervised learning models 552 may be trained using, for example, linear and radial basis function SVMs, logistic and ridge regression, conventional decision trees and gradient-boosted decision tree Extreme Gradient Boosting (XGBoost) models, as well as other machine learning models. The machine learning methods derived from the supervised learning model 552 may include limiting the various trained models to a model for stress detection and a model for stress type classification. In some embodiments, the models for stress detection and stress type classification are the same, while in other embodiments, the models for stress detection and stress type classification are different.

The machine learning methods derived from the supervised learning model 552 may further include extracting features from stress regions for overall stress level evaluation. Extracting features from stress may include taking average signal changes from the MA of sensors. The machine learning methods derived from the supervised learning model 552 may further include training and evaluating machine learning models including linear regression and SVM. The reduced size of the datasets of these models could prevent overfitting. The machine learning methods derived from the supervised learning model 552 could also include performing a brute-force examination of features to compare the contributions of physicochemical biomarkers.

During stressor classification, the machine learning methods derived from the supervised learning model 552 may further include a feature importance evaluation for each biomarker towards each stressor to evaluate each physicochemical sensor's contribution to the model. The biomarkers considered by the machine learning methods derived from the supervised learning model 552 may include glucose, lactate, UA, sodium, ammonium, potassium, and any relevant vital sign (e.g., pulse, GSR, skin temperature, etc.), in addition to other metabolites and electrolytes relevant to stress assessment. The feature importance evaluation may be conducted using a Shapley additive explanation (SHAP). Through SHAP analysis, the feature importance of each biomarker may indicate that these biomarkers play an important role in stressor classification.

The machine learning methods derived from the supervised learning model 552 may include an evaluation of state anxiety levels. The methods may include using a trained XGBoost regression model and predicting state anxiety levels. Such methods may include an evaluation of the relevance of each feature using SHAP analysis. Through SHAP analysis, a SHAP value could be determined for each feature, which can be indicative of the relative importance of each feature in the machine learning model. From such analysis, it may be determined which biomarkers play an important role in state anxiety level.

The machine learning methods derived from the supervised learning model 552 may include analyzing a stress response event as a whole to mimic questionnaire functionalities, because questionnaires tend to characterize state anxiety levels in a given time period based on subjective perception, rather than continuous dynamic stress change. The machine learning methods also may include extracting features from the stress region by taking mean signal changes from the moving average (MA) of sensor data rather than segmented at each timepoint. The machine learning methods performed to achieve the supervised learning model 552 may further include training a simple linear regression model with fewer features selected.

The machine learning methods derived from the supervised learning model 552 may yield a higher accuracy of stress response classification for stress/relaxation detection and a higher accuracy for stressor classification. The machine learning methods derived from the supervised learning model 552 could result in highly consistent overall accuracies across different individuals. For example, the methods can achieve a stress response classification accuracy of 99.2% for stress/relaxation detection and an accuracy of more than 98.0% for stressor classification.

Figure 5C:
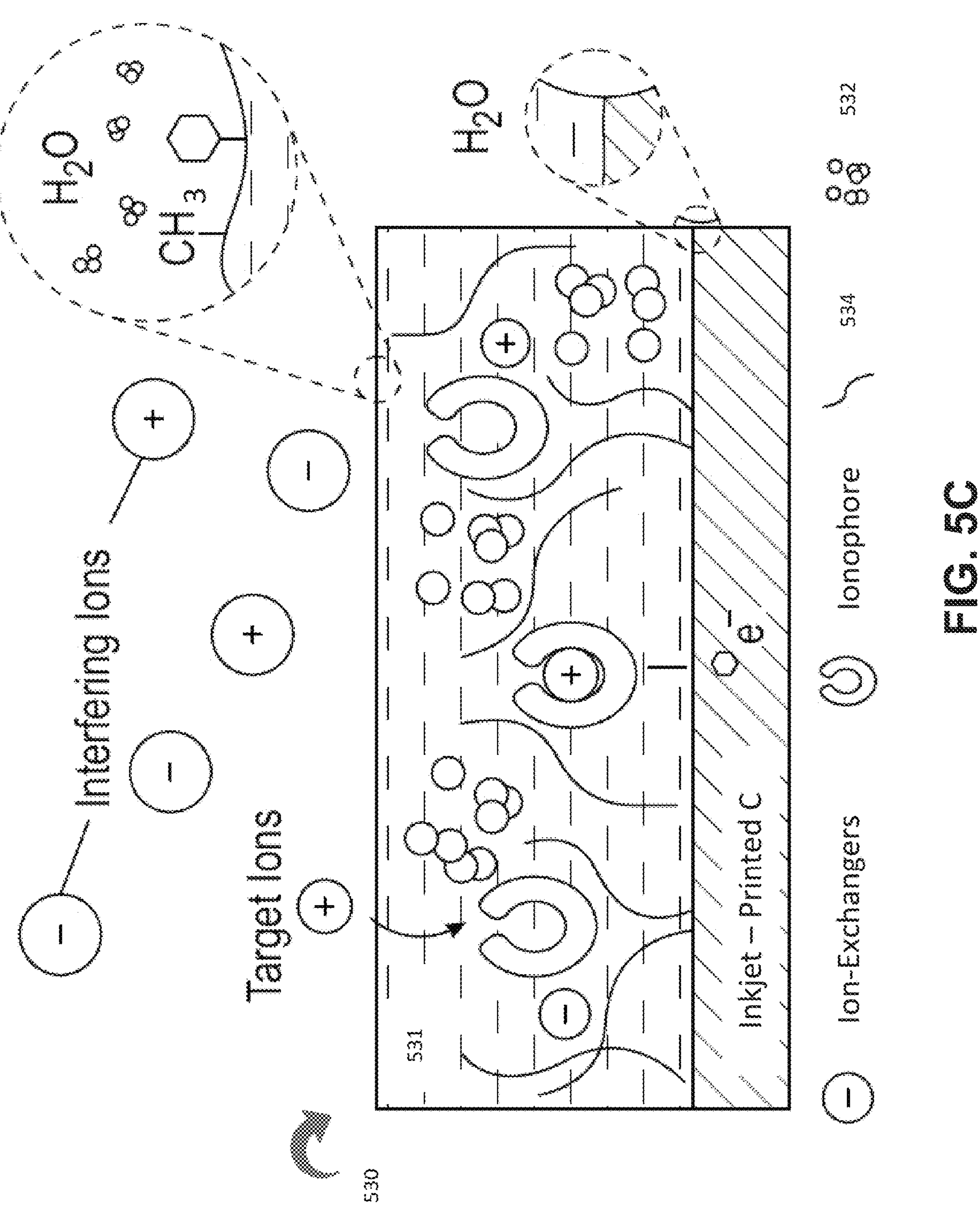
FIG. 5C is an example diagram of an ion-selective sensor (ISE), in accordance with various embodiments of the disclosed technology.

FIG. 5C is an example diagram of an ion-selective sensor (ISE) 530, in accordance with various embodiments of the disclosed technology. Existing conventional wearable ISEs are often based on PVC/DOS membranes and are plagued with potential drift of typically-2 mV per hour over time, which can be attributed to ionophore leaching and water formation below the ion-selective membrane 531. To address this issue during long-term operation, the present disclosure may include another analogous composite materials design strategy by introducing polystyrene-block-poly (ethylene butylene)-block-polystyrene (SEBS) 532 into the PVC 534; such composite shares a similar long-chain structure but can hold more methyl and phenyl groups at the sensor interface to promote hydrophobicity and mechanical strength. High hydrophobicity can suppress ionophore leaching and prevent a water layer from forming at the interface.

To fabricate ISEs 530, electrodes may be made from inkjet-printed carbon nanoparticles, which may be inert but may have a large surface area, such electrodes may be used without the need to deposit further ion-charge transducer materials. Ion-selective membranes 531 based on the PVC-SEBS 532, 534 matrix may be drop-casted onto the carbon electrode, and the SEBS 532 to PVC 534 may be evaluated to identify optimal stability. The optimized ISEs 530 may obtain prolonged stability of 100 hours of continuous operation in both standard solutions and human sweat samples with the potential value decaying less than 0.04 mV per hour (see, e.g., Table 2 below).

timodal monitoring may enable various personalized healthcare, stress, anxiety, and human performance monitoring applications, as discussed throughout this disclosure.

Figure 7:
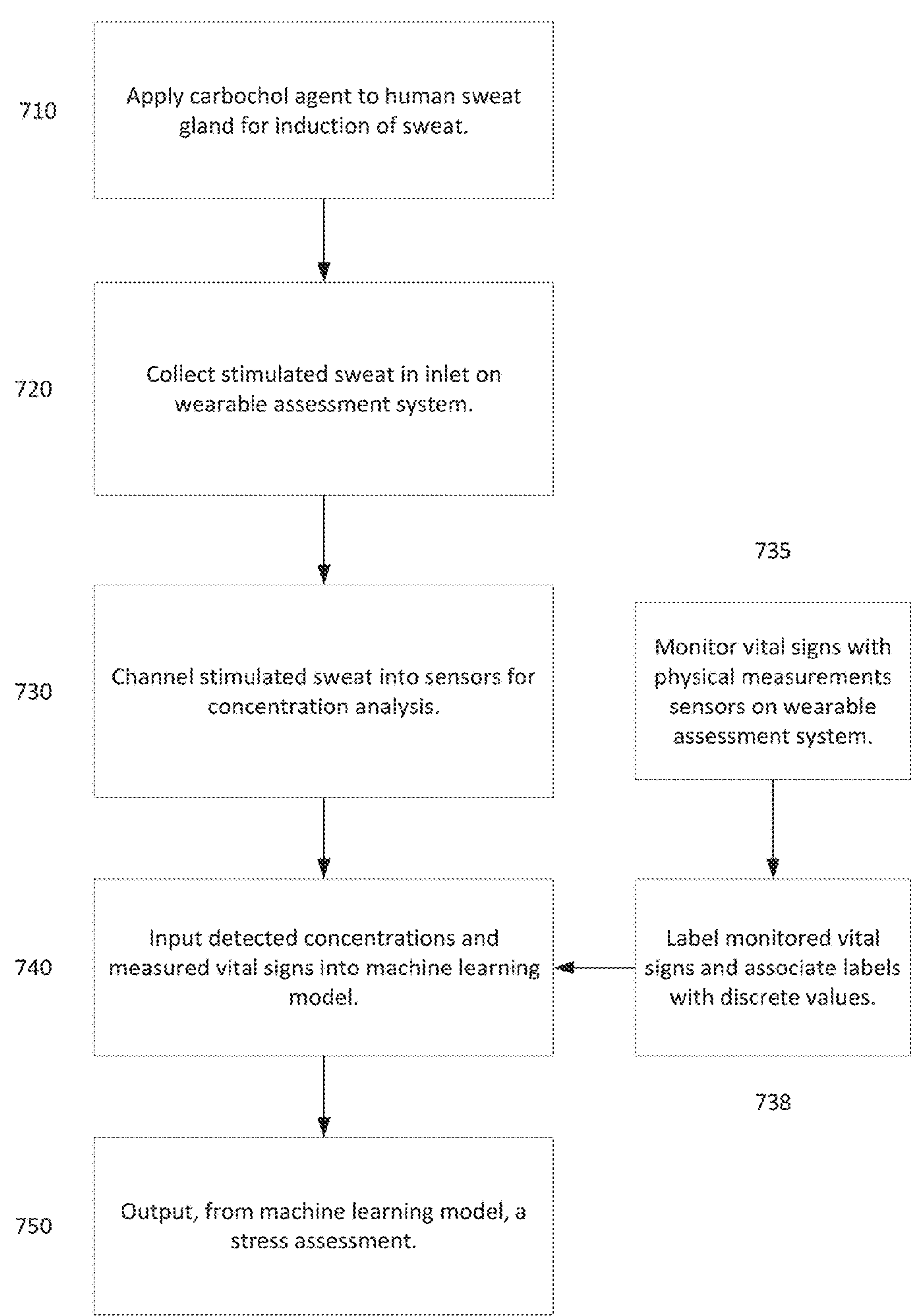
FIG. 7 is an example of a flow diagram showing a method for sweat induction and analysis, in accordance with various embodiments of the disclosed technology.

FIG. 7 is an example of a flow diagram showing a method for sweat induction and analysis, in accordance with various embodiments of the disclosed technology. First, a stimulating agent, e.g., carbachol, may be applied to a human sweat gland to induce a flow of sweat 710. The stimulating agent may be a carbagel, carbachol, carbachol hydrogel, or other agent that stimulates the flow of sweat. Second, the stimulated sweat is collected via an inlet on the wearable assessment system 720. The inlet may be located on the sweat microfluidics layer. Third, the sweat sample may be channeled from the inlet to the sensors, located on the sensor patch, for concentration analysis 730. At a similar time, the wearable assessment system may monitor vital signs with physical measurement sensors on the wearable assessment system 735. The output of the physical measurement sensors may be labeled and assigned values based on the monitored vital signs 738. The concentrations detected by the sensors in step 730 and the values from the monitored vital signs in step 738 may be input into a machine learning model 740 (which, as discussed, may be trained on known data sets during supervised learning, and subsequently applied with unknown outputs). Finally, the output, from the machine learning model, is produced as a stress assessment 750.

TABLE 2

List of sweat electrolyte sensors for on-body monitoring {PVC, polyvinyl chloride, DOS, bis(2-ethylhexyl) sebacate; LEG, laser-engraved graphene; o-NPOE, o-nitrophenyl octyl ether}.

| Analyte | Substrate | Functional materials | ISM matrix | Stability | Stability in sweat |
|---|---|---|---|---|---|
| $Na^+$ | Screen-printed carbon | Carbon | PVC/DOS | 2.8 mV $h^{-1}$ | 1 hour |
| $Na^+$, $K^+$ | Au | PEDOT:PSS | PVC/DOS | 2-3 mV $h^{-1}$ | 2 hours |
| $K^+$ | Glassy carbon | PEDOT:PSS | Silicone rubber/ PVC/DOS | 0.14 mV $min^{-1}$ | N/A |
| $K^+$ | Screen-printed carbon | Ferrocyanide/ PEDOT:PSS | PVC/DOS | 0.8 mV $h^{-1}$ | N/A |
| $K^+$ | Carbon/Graphite | Single-walled CNT | Poly(n-butylacrylate) | 0.19 mV $h^{-1}$ | N/A |
| $Na^+$ | Au | Au nanodendrites | PVC/DOS | 0.22 mV $h^{-1}$ | 2 hours |
| $K^+$, $Ca^{2+}$, $H^+$ | Graphene paper | Graphene paper | PVC/o-NPOE | 1.92-2.27 mV $h^{-1}$ | N/A |
| $NH_4^+$ | Screen-printed Ag | Screen-printed carbon | PVC/o-NPOE | N/A | 1 hour |
| $Na^+$, $K^+$ | PB analogues (Na—NiHCF, K—FeHCF) | PB analogues (Na—NiHCF, K—FeHCF) | PVC/o-NPOE or PVC/DOS | 10-50 mV $day^{-1}$ | N/A |
| $Na^+$, $K^+$, $NH_4^+$ | Inkjet carbon | Carbon nanoparticles | SEBS/PVC/DOS | 0.04 mV $h^{-1}$ | 100 hours |

Figure 5D:
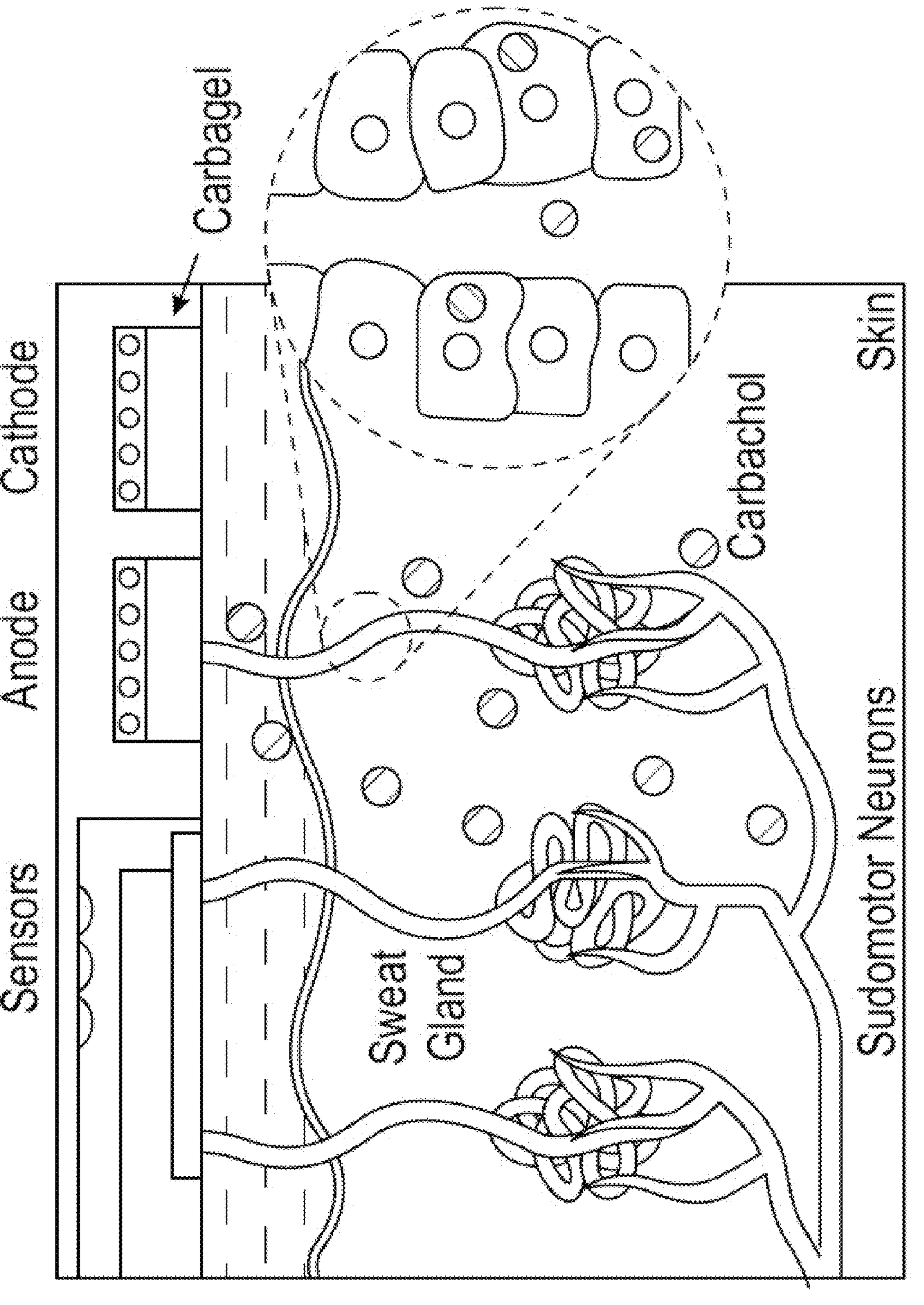
FIG. 5D is an example diagram of an on-body evaluation of the wearable assessment system for autonomous sweat induction and sampling, in accordance with various embodiments of the disclosed technology.

FIG. 5D is an example diagram of an on-body evaluation of the wearable assessment system for autonomous sweat induction and sampling, in accordance with various embodiments of the disclosed technology.

Figure 6:
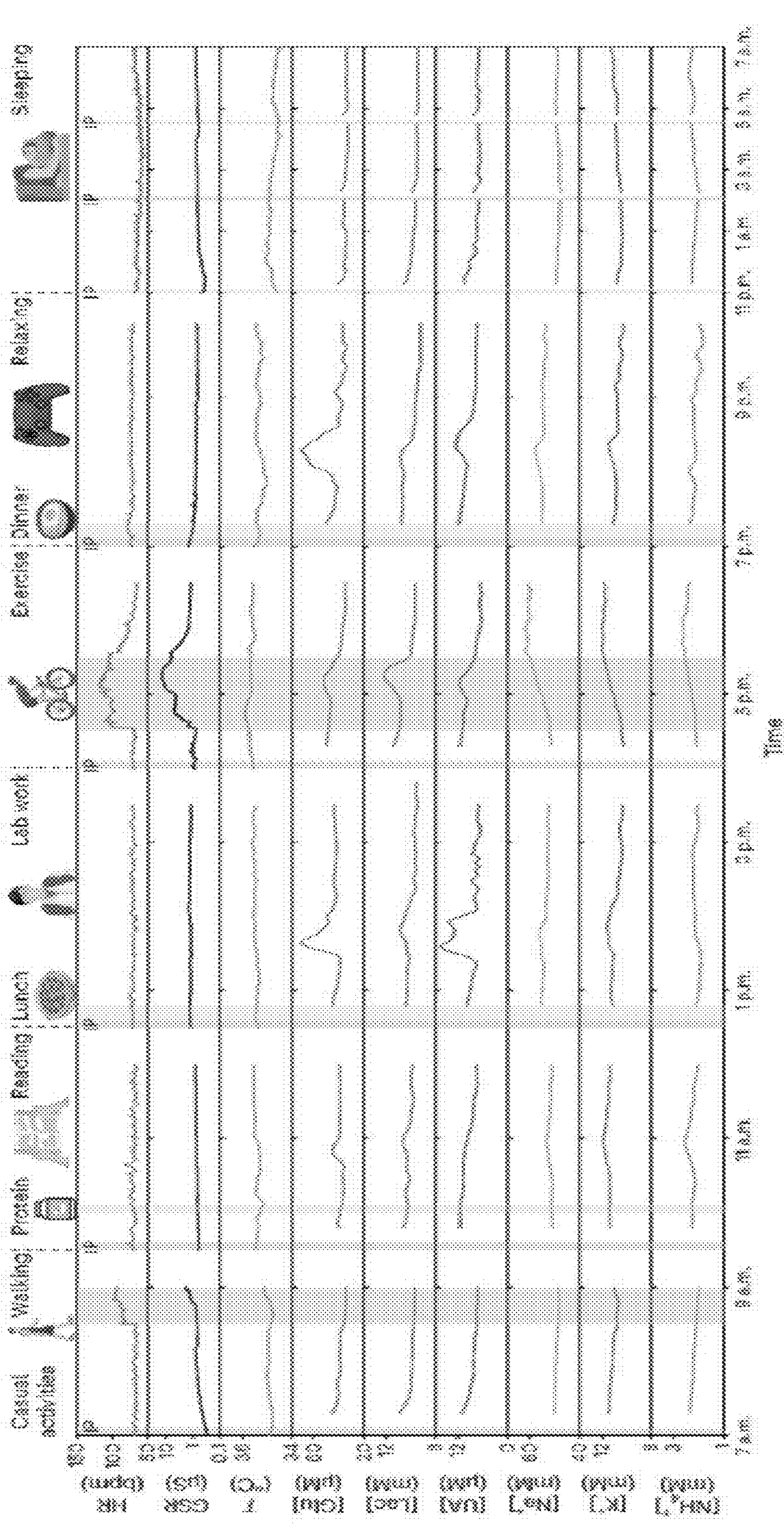
FIG. 6 is an example illustration of changes in biomarkers based on different activities over time, in accordance with various embodiments of the disclosed technology.

FIG. 6 is an example illustration of changes in biomarkers based on different activities over time, in accordance with various embodiments of the disclosed technology. Due to the long-term stability of wearable sweat biosensors, the wearable assessment system may enable long-term real-time (or near-real-time) continuous monitoring of physicochemical biomarkers. As illustrated in FIG. 6, the wearable assessment system may be able to record dynamic changes in concentrations of electrolytes, metabolites, and monitored vital signs over a given period (e.g., 24 hours) of activity involving casual and vigorous exercise, dietary intake, lab work, relaxing entertainment, and sleep (as examples). As depicted, glucose and UA levels may spike after food intake, indicating increased metabolic activities. During vigorous exercise, more significant increases in vascular activity and skin electrolyte/conductivity may be present, while stable output for both metabolites and vital signs may be present during sleep at night. Such capabilities of continuous mul- A wearable assessment system, as described in reference to FIGS. 1-7, above, may measure concentrations of many different biomarkers in addition to electrolytes, metabolites, and/or vital signs. For example, a wearable assessment system may measure the concentrations of all or any of the nine essential amino acids. Amino acids are organic compounds that are present in the human body and in food sources. Concentrations of amino acids may vary depending on many factors including dietary intake, genetic predisposition, gut microbiota, environmental factors, lifestyle factors including sleep and exercise, and other factors. The concentrations of amino acids present in human bodily fluids, including sweat and blood, can provide important information about the health of an individual. For example, elevated levels of branched-chain amino acids (BCAAs) including for example, leucine (Leu), isoleucine (Ile), and valine (Val) may be correlated with certain health conditions including obesity, insulin resistance, diabetes, cardiovascular disease, and pancreatic cancer. Deficiencies in amino acids, including, for example, arginine and cysteine, may indicate immune suppression and/or reduced immune-cell activation In another embodiment, a wearable assessment system may measure concentrations of amino acids in addition to other organic compounds, including vitamins and minerals. For example, imbalances with tryptophan (Trp), tyrosine (Tyr) and phenylalanine (Phe), which are needed to support neurotransmitters such as serotonin, dopamine, norepinephrine, and epinephrine, may indicate neurological and/or mental health conditions. Other metabolic indicators involving, for example, Leu, Phe, and vitamin D, may be linked with severity, vulnerability, and mortality related to viral infections including COVID-19. Other compounds, like glucose and uric acid may also be measured outside of the stress assessment context to determine risk of developing, and/or severity of, a particular health condition.

In another embodiment, amino acids, vitamins, and mineral concentrations may be measured to develop a personalized nutrition plan. After measurement of initial concentrations, a human patient may be advised to make dietary modifications to account for deficiencies and/or excesses of key amino acids, vitamins, and minerals. The human patients adherence to a nutritional plan and progress may be monitored continuously with the wearable assessment system.

As discussed throughout, stress and fatigue detection and evaluation may be made based on concentrations of relevant electrolytes and metabolites. An object model for stress and fatigue may be trained. For example, the object model may be trained with standard stress and fatigue questionnaires. Then, machine learning methods may be used to optimize detection and evaluation of stress and fatigue through electrolyte and metabolic analysis, using questionnaires as an object model. For example, a machine learning model may optimize which electrolytes and metabolites are most accurately correlated with stress and fatigue determinations. A machine learning model may further optimize the level of detected metabolites that correlate more accurately to noteworthy stress and fatigue related health conditions. A machine learning model may be leveraged to determine at which point a human patient is experiencing too much stress and fatigue to be effective in a given role.

In another embodiment a wearable assessment system may detect and measure drug compounds present in the sweat sample. Drug compounds may be measured to assess compliance with a drug treatment regimen. Drug compounds may also be measured to assess successful metabolization of a treatment drug. Drug compounds may also be measured to determine the risk and/or severity of drug toxicity due to a drug treatment regimen.

In another embodiment, the wearable assessment system may measure the concentration of certain hormones. In another embodiment, the wearable assessment system may measure the concentration of antibodies present in a human patient which may indicate an infection, the degree of immune response to a viral, bacterial, or fungal agent, an autoimmune disease, or another health condition.

A wearable assessment system may employ various power sources. For example, in one embodiment, a wearable assessment system may be equipped with a lightweight battery. In another embodiment, the wearable assessment system may be wired to a smart device's power supply. In another embodiment, the wearable assessment system may leverage a biofluid powering system to power the device with the collected sweat flow itself. In another embodiment, the wearable assessment system may be powered with a small solar panel. In another embodiment, the wearable assessment system may be powered by human motion.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A wearable stress response assessment system, comprising:

a multilayer sweat sensor patch adapted to adhere to and induce sweat production from human skin, wherein the multilayer sweat sensor patch further comprises:

a carbochol hydrogel-loaded sweat-stimulation electrode;

a hydrogel-loaded sweat-stimulation electrode;

three enzymatic biosensors; and three ion-selective sensors (ISEs);

wherein the carbochol hydrogel-loaded sweat-stimulation electrode and the hydrogel-loaded sweat-stimulation electrode are integrated into a skin-interfaced laser-engraved microfluidic component, wherein the skin-interfaced laser-engraved microfluidic component collects an induced sweat sample for analysis;

wherein the three enzymatic biosensors are integrated into a metabolite detection logical circuit that is further integrated within the sensor patch, wherein each enzymatic biosensor is configured to identify concentrations of one of glucose, lactate, and uric acid (UA) in the collected sweat sample; and wherein the three ion-selective sensors (ISEs) are integrated into a electrolyte detection logical circuit that is further integrated within the sensor patch, wherein each ion-selective sensor is configured to identify concentrations of one of $Na^+$, $K^+$, and $NH4^+$ in the collected sweat sample;

wherein the three enzymatic biosensors each comprise:

an electrodeposited gold nanoparticles layer;

an electrodeposited Prussian blue transduction layer;

an electrodeposited nickel hexacyanoferrate (NiHCF) protection layer; and an enzyme layer in a glutaraldehyde-crosslinked bovine serum (BSA) matrix wherein the sweat sensor patch further comprises:

a top layer fabricated through serial inkjet printing of silver and carbon;

a bottom layer fabricated through serial inkjet printing of silver and carbon; and a middle polydimethylsiloxane (PDMS)-based airgap layer, wherein the middle polydimethylsiloxane (PDMS)-based airgap layer is spin-coated between the top and bottom layers wherein the three ion-selective sensors (ISEs) comprise:

a carbon layer; and a polystyrene-block-poly (ethylene butylene)-block-polystyrene (SEBS)-polyvinyl chloride (PVC)/bis(2-ethylhexyl) sebacate (DOS)-ionophore/lipophilic anionic sites mixture based membrane layer.

2. The wearable stress assessment system of claim 1, further comprising a skin-interfaced indicator logical circuit that comprises:

a capacitive pulse sensor configured to detect signals representative of a human subject's pulse waveform;

a resistive galvanic skin response (GSR) sensor configured to detect signals representative of a human subject's GSR level; and a skin temperature sensor configured to detect signals representative of a human subject's skin temperature.

3. The wearable stress assessment system of claim 1, further comprising a smart device, wherein the smart device analyzes the detected metabolite concentrations, and the detected electrolyte concentrations, and displays a stress assessment based on the analyzed metabolite concentrations and analyzed electrolyte concentrations.

4. The wearable stress assessment system of claim 3, wherein the stress assessment is determined using machine learning methods.

5. The wearable stress assessment system of claim 1, further comprising an in situ signal processing and wireless communication module.

6. The wearable stress assessment system of claim 1, wherein the three enzymatic biosensors further comprise a diffusion-limiting membrane layer that further tunes metabolite detections ranges for high concentration detection.

* * * * *